(12) United States Patent
Rojkjaer

(10) Patent No.: US 7,291,587 B2
(45) Date of Patent: Nov. 6, 2007

(54) PHARMACEUTICAL COMPOSITION COMPRISING FACTOR VII POLYPEPTIDES AND TAFI POLYPEPTIDES

(75) Inventor: Rasmus Rojkjaer, Gentofte (DK)

(73) Assignee: Novo Nordisk HealthCare A/G, Zurich (CH)

(*) Notice: Subject to any disclaimer, the term of this patent is extended or adjusted under 35 U.S.C. 154(b) by 655 days.

(21) Appl. No.: 10/290,814

(22) Filed: Nov. 8, 2002

(65) Prior Publication Data

US 2003/0118574 A1  Jun. 26, 2003

Related U.S. Application Data

(60) Provisional application No. 60/333,672, filed on Nov. 27, 2001.

(30) Foreign Application Priority Data

Nov. 9, 2001 (DK) ............................ 2001 01664

(51) Int. Cl.
*A61K 38/00* (2006.01)
(52) U.S. Cl. .................... 514/2; 514/18; 424/94.1
(58) Field of Classification Search ............. 514/2, 514/18; 424/94.1
See application file for complete search history.

(56) References Cited

U.S. PATENT DOCUMENTS

| | | | |
|---|---|---|---|
| 5,206,161 A | 4/1993 | Drayna et al. ............... 435/212 |
| 5,364,934 A | 11/1994 | Drayna et al. ............. 536/23.2 |
| 5,474,901 A | 12/1995 | Drayna et al. ............... 435/7.4 |
| 5,593,674 A | 1/1997 | Drayna et al. ............ 424/94.63 |
| 5,672,496 A | 9/1997 | Fayerman et al. .......... 435/212 |
| 5,866,122 A | 2/1999 | Turecek et al. ........... 424/94.64 |
| 6,808,927 B2 * | 10/2004 | Greenfield et al. ....... 424/94.63 |
| 6,825,323 B2 | 11/2004 | Hess |
| 6,838,432 B2 * | 1/2005 | Taylor et al. .................... 514/2 |
| 7,015,193 B2 * | 3/2006 | Butenas et al. ................. 514/2 |
| 2002/0177560 A1 * | 11/2002 | Greenfield et al. ........... 514/18 |
| 2003/0040480 A1 | 2/2003 | Rojkjaer |
| 2003/0054018 A1 | 3/2003 | Hedner |
| 2003/0073638 A1 | 4/2003 | Kjalke |
| 2003/0092627 A1 | 5/2003 | Petersen et al. |
| 2003/0109446 A1 | 6/2003 | Rojkjaer |
| 2003/0118580 A1 | 6/2003 | Rojkjaer |
| 2003/0118582 A1 | 6/2003 | Rojkjaer |
| 2003/0119723 A1 | 6/2003 | Rojkjaer |
| 2003/0119741 A1 | 6/2003 | Rojkjaer |
| 2003/0119743 A1 | 6/2003 | Rojkjaer |
| 2003/0124118 A1 | 7/2003 | Rojkjaer |
| 2003/0125256 A1 | 7/2003 | Rojkjaer |
| 2003/0199444 A1 | 10/2003 | Knudsen |
| 2003/0203845 A1 | 10/2003 | Knudsen |
| 2004/0006020 A1 | 1/2004 | Rojkjaer |
| 2004/0006021 A1 | 1/2004 | Rojkjaer |
| 2004/0258690 A1 | 12/2004 | Rojkjaer |

FOREIGN PATENT DOCUMENTS

| | | |
|---|---|---|
| EP | 0082182 B1 | 5/1982 |
| EP | 0225160 B1 | 11/1986 |
| WO | WO93/06855 A1 | 4/1993 |
| WO | WO98/35988 A1 | 8/1998 |
| WO | WO98/58661 A1 | 12/1998 |
| WO | WO 00/61727 A2 | 10/2000 |
| WO | WO 00/61727 A3 | 10/2000 |
| WO | WO 00/66717 A1 | 11/2000 |
| WO | WO 01/83725 A1 | 11/2001 |

OTHER PUBLICATIONS

Bajzar et al., Blood, vol. 88, No. 6, pp. 2093-2100 (1996).
Eaton et al., The Journal of Biological Chemistry, vol. 266, No. 32, pp. 21833-21838 (1991).
Mosnier et al., Thrombosis and Haemostasis, vol. 86, pp. 1035-1039 (2001).
Nesheim et al., Thrombosis and Haemostasis, vol. 78, No. 1, pp. 386-391 (1997).
Wang et al., The Journal of Biological Chemistry, vol. 269, No. 22, pp. 15937-15944 (1994).
Roberts et al., Seminars in Hematology, 41(1—Suppl 1):101-108 (2004).
NovoSeven® (Coagulation Factor VIIa (Recombinant)) US FDA Package.
Amaral et al., Intensive Care Med., 30:1032-1040 (2004).
Zeerleder et al., Chest, 128:2864-2875 (2005).

* cited by examiner

*Primary Examiner*—Cecilia Tsang
*Assistant Examiner*—Maury Audet
(74) *Attorney, Agent, or Firm*—Shelby J. Walker

(57) ABSTRACT

The present invention relates to a composition comprising factor VII or a factor VII-related polypeptide, and TAFI or a TAFI-related polypeptide, and the use thereof for treating bleeding episodes.

68 Claims, 2 Drawing Sheets

Figure 1:
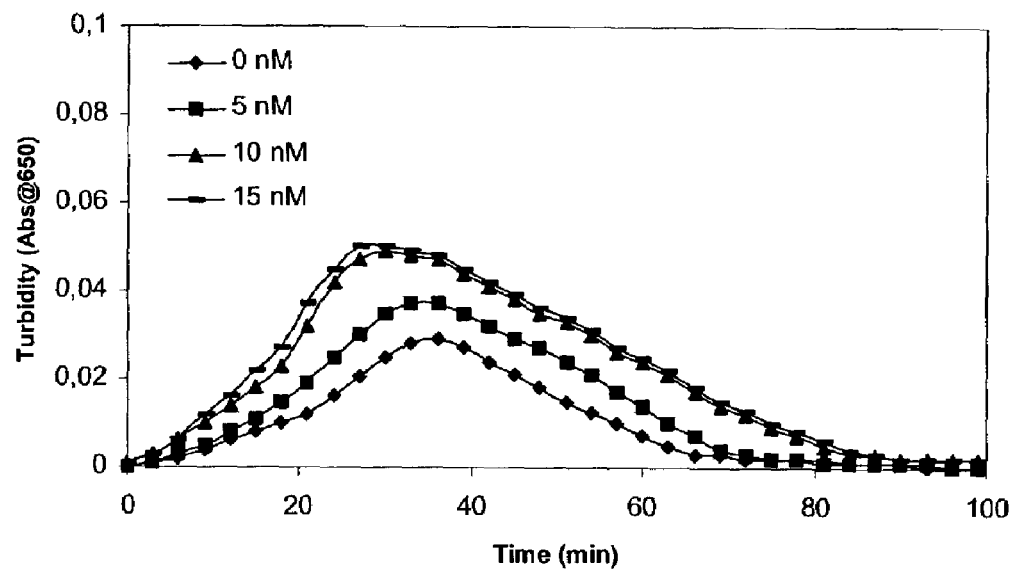

PHARMACEUTICAL COMPOSITION COMPRISING FACTOR VII POLYPEPTIDES AND TAFI POLYPEPTIDES

CROSS-REFERENCE TO RELATED APPLICATIONS

This application claims priority under 35 U.S.C. 119 of Danish application no. PA 2001 01664 filed Nov. 9, 2001 and U.S. application Ser. No. 60/333,672 filed Nov. 27, 2001, the contents of which are fully incorporated herein by reference.

FIELD OF THIS INVENTION

The present invention relates to a pharmaceutical composition comprising factor VII or a factor VII-related polypeptide and TAFI or a TAFI-related polypeptide. The invention also relates to the use of a combination of a factor VII or a factor VII-related polypeptide and a TAFI or a TAFI-related polypeptide for the manufacture of a medicament for treatment of subjects suffering from bleeding episodes, or prevention hereof. The invention also relates to a method for treatment of bleeding episodes in subjects and to a method for enhancing clot formation in a subject. The present invention also relates to kits comprising these compounds.

BACKGROUND OF THE INVENTION

Haemostasis is initiated by the formation of a complex between tissue factor (TF) being exposed to the circulating blood following an injury to the vessel wall, and FVIIa which is present in the circulation in an amount corresponding to about 1% of the total FVII protein mass. This complex is anchored to the TF-bearing cell and activates FX into FXa and FIX into FIXa on the cell surface. FXa activates prothrombin to thrombin, which activates FVIII, FV, FXI and FXIII. Furthermore, the limited amount of thrombin formed in this initial step of haemostasis also activates the platelets. Following the action of thrombin on the platelets these change shape and expose charged phospholipids on their surface. This activated platelet surface forms the template for the further FX activation and the full thrombin generation. The further FX activation on the activated platelet surface occurs via a FIXa-FVIIIa complex formed on the surface of the activated platelet, and FXa then converts prothrombin into thrombin while still on the surface. Thrombin then converts fibrinogen into fibrin which is insoluble and which stabilizes the initial platelet plug. This process is compartmentalized, i.e., localised to the site of TF expression or exposure, thereby minimizing the risk of a systemic activation of the coagulation system. The insoluble fibrin forming the plug is furthermore stabilised by FXIII-catalysed cross-linking of the fibrin fibres.

FVIIa exists in plasma mainly as a single-chain zymogen, which is cleaved by FXa into its two-chain, activated form, FVIIa. Recombinant activated factor VIIa (rFVIIa) has been developed as a pro-haemostatic agent. The administration of rFVIIa offers a rapid and highly effective pro-haemostatic response in haemophilic subjects with bleedings who cannot be treated with coagulation factor products due to antibody formation. Also bleeding subjects with a factor VII deficiency or subjects having a normal coagulation system but experiencing excessive bleeding can be treated successfully with FVIIa. In these studies, no unfavourable side effects of rFVIIa (in particular the occurrence of thromboembolism) has been encountered.

Extra exogenously administered FVIIa increases the formation of thrombin on the activated platelet surface. This occurs in haemophiliac subjects lacking FIX or FVIII and therefore missing the most potent pathway for full thrombin formation. Also in the presence of a lowered number of platelets or platelets with a defect function, extra FVIIa increases the thrombin formation.

Commercial preparations of recombinant human FVIIa are sold as NOVOSEVEN® (Novo Nordiak A/S. Denmark). NOVOSEVEN® is indicated for treatment of bleeding episodes in haemophilia A and B patients. NOVOSEVEN® is the only recombinant FVIIa available on the market for effective and reliable treatment of bleeding episodes.

Thrombin-activatable-fibrinolysis-inhibitor (TAFI) is a plasma carboxypeptidase with specificity for carboxyl-terminal arginine and lysine residues that acts as a potent inhibitor of fibrinolysis (Nesheim et al., Thromb. Haemost. 78:386, 1997). It is identical to the previously cloned plasma carboxypeptidase B (Eaton et al., J. Biol.Chem 269:21833, 1991) and the previously isolated carboxypeptidase U (Wang et al., J. Biol. Chem. 269:15937, 1994). This single chain 60.000 M polypeptide circulates in plasma at concentrations of about 70 nM (Bajzar et al., Blood 88:2093, 1997), and undergoes limited proteolysis in the presence of thrombin, which leads to its activation. The active carboxypeptidase, activated TAFI (TAFIa), catalyzes the removal of carboxy-terminal lysines and arginines, in the context of a fibrin clot. Since these residues are essential for the assembly of the fibrinolytic proteins, their removal down-regulates fibrinolysis.

It is well known that subjects who bleed excessively in association with surgery or major trauma and need blood transfusions develop more complications than those who do not experience any bleeding. However, also moderate bleedings requiring the administration of human blood or blood products (platelets, leukocytes, plasma-derived concentrates for the treatment of coagulation defects, etc.) may lead to complications associated with the risk of transferring human viruses (hepatitis, HIV, parvovirus, and other, by now unknown viruses). Extensive bleedings requiring massive blood transfusions may lead to the development of multiple organ failure including impaired lung and kidney function. Once a subject has developed these serious complications a cascade of events involving a number of cytokines and inflammatory reactions is started making any treatment extremely difficult and unfortunately often unsuccessful. Therefore a major goal in surgery as well as in the treatment of major tissue damage is to avoid or minimise the bleeding. To avoid or minimise such bleeding it is of importance to ensure the formation of stable and solid haemostatic plugs that are not easily dissolved by fibrinolytic enzymes. Furthermore, it is of importance to ensure quick and effective formation of such plugs or clots.

Today, subjects experiencing bleeding episodes, including trauma victims and subjects bleeding in association with surgery, are often treated with several injections or infusions of FVIIa since the short half-life of FVIIa (2.5 hours) may require more than one administration to maintain a certain level of haemostatic ability. A faster arrest of bleedings would be an important benefit to such subjects. So would a reduction in the number of administrations needed to stop bleeding and maintain haemostasis.

European Patent No. 225.160 (Novo Nordisk) concerns compositions of FVIIa and methods for the treatment of bleeding disorders not caused by clotting factor defects or clotting factor inhibitors.

European Patent No. 82.182 (Baxter Travenol Lab.) concerns a composition of factor VIIa for use in counteracting deficiencies of blood clotting factors or the effects of inhibitors to blood clotting factors in a subject.

International Patent Publication No. WO 93/06855 (Novo Nordisk) concerns the topical application of FVIIa.

U.S. Pat. Nos. 5,206,161, 5,364,934, and 5,593,674 concern isolated monomeric human carboxypeptidase B (PCPB), expression vector and host cell for making PCPB, and a method for coagulating blood comprising adding PCPB to the blood.

There is still a need in the art for improved treatment of subjects experiencing bleeding episodes, including subjects where the bleeding episodes are due to surgery, trauma, or other forms of tissue damage; induced coagulophathy, including coagulopathy in multi-transfused subjects; congenital or acquired coagulation or bleeding disorders, including diminished liver function ("liver disease"); defective platelet function or decreased platelet number; lacking or abnormal essential clotting "compounds" (e.g., platelets or von Willebrand factor protein); increased fibrinolysis; anticoagulant therapy or thrombolytic therapy; or stem cell transplantation.

There remains a need in the art for an improved, reliable and widely applicable method of enhancing coagulation, enhancing or ensuring formation of stable haemostatic plugs, or enhancing convenience for the treated subject, or achieving full haemostasis in subjects, in particular in subjects having an impaired thrombin generation. There is also a need for methods wherein the time to bleeding arrest is shortened.

SUMMARY OF THE INVENTION

One object of the present invention is to provide compositions, which can effectively be used in the treatment or prophylaxis of bleeding episodes and coagulation disorders.

A second object of the present invention is to provide compositions in single-unit dosage form, which can effectively be used in the treatment or prophylaxis of bleeding episodes or as a procoagulant. Another object of the present invention is to provide compositions, methods of treatment or kits exhibiting a synergistic effect.

A further object of the present invention is to provide compositions, methods of treatment or kits exhibiting no substantial side effects, such as a high level of systemic activation of the coagulation system.

Other objects of the present invention will become apparent upon reading the present description.

In a first aspect the invention provides a pharmaceutical composition comprising factor VII or a factor VII-related polypeptide, and TAFI or a TAFI-related polypeptide.

In a second aspect, the invention provides a kit of parts containing a treatment for bleeding episodes comprising
   a) An effective amount of a preparation of factor VII or a factor VII-related polypeptide and a pharmaceutically acceptable carrier in a first-unit dosage form;
   b) An effective amount of a preparation of TAFI or a TAFI-related polypeptide and a pharmaceutically acceptable carrier in a second-unit dosage form; and
   c) Container means for containing said first and second dosage forms.

In a third aspect, the invention provides the use of factor VII or a factor VII-related polypeptide in combination with a TAFI or a TAFI-related polypeptide for the manufacture of a medicament for treating bleeding episodes in a subject. In a further aspect, the invention provides the use of a composition as described in any one of claims 1 to 18, for the manufacture of a medicament for treating bleeding episodes in a subject.

In different embodiments thereof, the medicaments are for reducing time needed to obtain full haemostasis, reducing time needed to maintain haemostasis, reducing clotting time, prolonging the clot lysis time, and increasing clot strength.

In different embodiments, the medicaments are for treatment of subjects experiencing bleeding episodes due to surgery, trauma, or other forms of tissue damage; coagulophathy, including coagulopathy in multi-transfused subjects; congenital or acquired coagulation or bleeding disorders, including decreased liver function ("liver disease"); defective platelet function or decreased platelet number; lacking or abnormal essential clotting "compounds" (e.g., platelets or von Willebrand factor protein); increased fibrinolysis; anticoagulant therapy or thrombolytic therapy; stem cell transplantation. In one series of embodiments, the bleedings occur in organs such as the brain, inner ear region, eyes, liver, lung, tumour tissue, gastrointestinal tract; in another series of embodiments, it is diffuse bleeding, such as in haemorrhagic gastritis and profuse uterine bleeding. In another series of embodiments, the bleeding episodes are bleeding in connection with surgery or trauma in subjects having acute haemarthroses (bleedings in joints), chronic haemophilic arthropathy, haematomas, (e.g., muscular, retroperitoneal, sublingual and retropharyngeal), bleedings in other tissue, haematuria (bleeding from the renal tract), cerebral haemorrhage, surgery (e.g., hepatectomy), dental extraction, and gastrointestinal bleedings (e.g., UGI bleeds). In one embodiment, the medicament is for treating bleeding episodes due to trauma, or surgery, or lowered count or activity of platelets, in a subject.

In a further aspect, the invention provides a method for treating bleeding episodes in a subject, the method comprising administering to a subject in need thereof a first amount of a preparation of factor VII or a factor VII-related polypeptide and a second amount of a preparation of TAFI or a TAFI-related polypeptide, wherein the first and second amount together are effective to treat bleedings.

In a further aspect, the invention provides a method for reducing clotting time in a subject, the method comprising administering to a subject in need thereof a first amount of a preparation of factor VII or a factor VII-related polypeptide and a second amount of a preparation of TAFI or a TAFI-related polypeptide wherein the first and second amount together are effective to reduce clotting time.

In a further aspect, the invention provides a method to enhance haemostasis in a subject, the method comprising administering to a subject in need thereof a first amount of a preparation of factor VII or a factor VII-related polypeptide and a second amount of a preparation of TAFI or a TAFI-related polypeptide wherein the first and second amount together are effective to enhance haemostasis.

In a further aspect, the invention provides a method for prolonging the clot lysis time in a subject, the method comprising administering to a subject in need thereof a first amount of a preparation of factor VII or a factor VII-related polypeptide and a second amount of a preparation of TAFI or a TAFI-related polypeptide wherein the first and second amount together are effective to prolong the clot lysis time.

In a further aspect, the invention provides a method for increasing clot strength in a subject, the method comprising administering to a subject in need thereof a first amount of a preparation of factor VII or a factor VII-related polypeptide and a second amount of a preparation of TAFI or a TAFI-related polypeptide wherein the first and second amount together are effective to increase clot strength.

In one series of embodiments of the methods, the factor VII or factor VII-related polypeptide and the TAFI or TAFI-related polypeptide are administered in single-unit dosage form.

In another series of embodiments the factor VII or factor VII-related polypeptide and the TAFI or TAFI-related polypeptide are administered in the form of a first-unit dosage form comprising a preparation of factor VII or a factor VII-related polypeptide and a second-unit dosage form comprising a preparation of TAFI or a TAFI-related polypeptide. In a series of embodiments thereof, the first-unit dosage form and the second-unit dosage form are administered with a time separation of no more than 15 minutes.

In a further aspect, the invention provides a kit containing a treatment for bleeding episodes comprising d) An effective amount of factor VII or a factor VII-related polypeptide and an effective amount of TAFI or a TAFI-related polypeptide and a pharmaceutically acceptable carrier in a single-unit dosage form; and e) Container means for containing said single-unit dosage form.

In one series of embodiments of the invention, the factor VII or factor VII-related polypeptide is a factor VII-related polypeptide. In one series of embodiments of the invention the factor VII-related polypeptide is a factor VII amino acid sequence variant. In one embodiment the ratio between the activity of the factor VII-related polypeptide and the activity of native human factor VIIa (wild-type FVIIa) is at least about 1.25 when tested in the "In Vitro Hydrolysis Assay" as described in the present description.

In one series of embodiments of the invention the factor VII or factor VII-related polypeptide is factor VII. In one embodiment said factor VII is human factor VII. In one embodiment the factor VII is bovine, porcine, canine, equine, murine or salmon factor VII. In another embodiment the factor VII is recombinantly made. In another embodiment the factor VII is derived from plasma. In a preferred embodiment the factor VII is recombinant human factor VII. In one series of embodiments of the invention the factor VII or factor VII-related polypeptide is in its activated form. In one preferred embodiment of the invention the factor VII is recombinant human factor VIIa.

In one series of embodiments the TAFI or TAFI-related polypeptide is a TAFI-related polypeptide. In one embodiment the TAFI-related polypeptide is a TAFI amino acid sequence variant. In one embodiment the ratio between the activity of said TAFI-related polypeptide and the activity of native human plasma TAFI (wild-type TAFI) is at least about 1.25 when tested in the "TAFI assay" as described in the present description. In one embodiment the TAFI or TAFI-related polypeptide is a TAFI polypeptide. In one embodiment the TAFI is human TAFI. In one embodiment the TAFI is bovine, porcine, canine, equine, murine or rat TAFI. In a preferred embodiment the TAFI is recombinantly made. In another embodiment the TAFI is derived from plasma In a preferred embodiment the TAFI is recombinant human TAFI. In one series of embodiments of the invention the TAFI or TAFI-related polypeptide is in its activated form. In one embodiment the TAFI-related polypeptide is a fragment of TAFI. In one embodiment the TAFI-related polypeptide is a hybrid TAFI polypeptide, e.g., a porcine/human hybrid. In one embodiment, the TAFI is human activated TAFI (TAFIa).

In one embodiment the factor VII or factor VII-related polypeptide and the TAFI or factor-XI related polypeptide are present in a ratio by mass of between about 100:1 and about 1:100 (w/w factor VII:TAFI).

In one embodiment, the factor VII-related polypeptides are amino acid sequence variants having no more than 20 amino acids replaced, deleted or inserted compared to wild-type factor VII (i.e., a polypeptide having the amino acid sequence disclosed in U.S. Pat. No. 4,784,950), In another embodiment, the factor VII variants have no more than 15 amino acids replaced, deleted or inserted; in other embodiments, the factor VII variants have no more than 10 amino acids, such as 8, 6, 5, or 3 amino acids, replaced, deleted or inserted compared to wild-type factor VII. In one embodiment, the factor VII variants are selected from the list of L305V-FVIIa, L305V/M306D/D309S-FVIIa, L305I-FVIIa, L305T-FVIIa, F374P-FVIIa, V158T/M298Q-FVIIa, V158D/E296V/M298Q-FVIIa, K337A-FVIIa, M298Q-FVIIa, V158D/M298Q-FVIIa, L305V/K337A-FVIIa, V158D/E296V/M298Q/L305V-FVIIa, V158D/E296V/M298Q/K337A-FVIIa, V158D/E296V/M298Q/L305V/K337A-FVIIa, K157A-FVII, E296V-FVII, E296V/M298Q-FVII, V158D/E296V-FVII, V158D/M298K-FVII, and S336G-FVII In a further embodiment, the factor VII-related polypeptides have increased tissue factor-independent activity compared to native human coagulation factor VIIa. In another embodiment, the increased activity is not accompanied by changes in the substrate specificity. In another embodiment of the invention, the binding of the factor VII-related polypeptides to tissue factor are not impaired and the factor VII-related polypeptides have at least the activity of wild-type factor VIIa when bound to tissue factor.

In a preferred embodiment, the factor VII or factor VII-related polypeptide and the TAFI or TAFI-related polypeptide are recombinant human factor VIIa and recombinant human TAFI.

In one embodiment, the clotting time is reduced in mammalian blood. In another embodiment the haemostasis is enhanced in mammalian blood. In another embodiment the clot lysis time is prolonged in mammalian blood. In another embodiment the clot strength is increased in mammalian blood. In one embodiment, the mammalian blood is human blood. In another embodiment, the mammalian blood is normal human blood; in one embodiment, the blood is blood from a subject having an impaired thrombin generation. In one embodiment, the blood is blood from a subject having a deficiency of one or more coagulation factors; in another embodiment, the blood is blood from a subject having inhibitors against one or more coagulation factors; in one embodiment, the blood is from a subject having a lowered concentration of fibrinogen; in one embodiment, the blood is TAFI-deficient human blood. In one series of embodiments, the blood is plasma.

In one embodiment of the invention, the factor VII or factor VII-related polypeptide and the TAFI or TAFI-related polypeptide are the sole haemostatic agents contained in the composition. In another embodiment, the factor VII or factor VII-related polypeptide and the TAFI or TAFI-related polypeptide are the sole active haemostatic agents contained in the composition. In another embodiment, the factor VII or factor VII-related polypeptide and the TAFI or TAFI-related polypeptide are the sole coagulation factors administered to the subject. In one embodiment of the invention, the factor VII or factor VII-related polypeptide and the TAFI or TAFI-related polypeptide are the sole active agents administered to the patient. In one embodiment, the composition is substantially free of thrombin or prothrombin; in another embodiment, the composition is substantially free of FX; in another embodiment, the composition is substantially free of FXa.

In another embodiment, the pharmaceutical composition is formulated for intravenous administration, preferably injection or infusion, in particular injection. In one embodiment, the composition contains at least one pharmaceutical acceptable excipients or carrier.

In one embodiment of the invention, the composition is in single-unit dosage form wherein the single-unit dosage form contains both coagulation factors. In one embodiment of the invention, the composition is in the form of a kit-of-parts comprising a preparation of factor VII or a factor VII-related polypeptide as a first-unit dosage form and a preparation of TAFI or a TAFI-related polypeptide as a second-unit dosage form, and comprising container means for containing said first and second-unit dosage forms. In one embodiment the composition or kit, as applicable, further contains directions for the administration of the composition or separate components, respectively.

In one embodiment of the invention, the factor VII or factor VII-related polypeptide and the TAFI or TAFI-related polypeptide are administered in single-dosage form. In one embodiment of the invention, the factor VII or factor VII-related polypeptide and the TAFI or TAFI-related polypeptide are administered in the form of a first-unit dosage form comprising a preparation of factor VII or a factor VII-related polypeptide and a second-unit dosage form comprising a preparation of TAFI or a TAFI-related polypeptide.

In one embodiment of the invention, the factor VII or factor VII-related polypeptide and the TAFI or TAFI-related polypeptide are administered simultaneously. In another embodiment, the factor VII or factor VII-related polypeptide and the TAFI or TAFI-related polypeptide are administered sequentially. In one embodiment, the factor VII or factor VII-related polypeptide and the TAFI or TAFI-related polypeptide are administered with a time separation of no more than 15 minutes, preferably 10, more preferred 5, more preferred 2 minutes. In one embodiment, the factor VII or factor VII-related polypeptide and the TAFI or TAFI-related polypeptide are administered with a time separation of up to 2 hours, preferably from 1 to 2 hours, more preferred up to 1 hour, more preferred from 30 minutes to 1 hour, more preferred up to 30 minutes, more preferred from 15 to 30 minutes.

In one embodiment, the effective amount of the factor VII or factor VII-related polypeptide is an amount from about 0.05 mg/day to about 500 mg/day (70-kg subject). In one embodiment, the effective amount of a preparation of TAFI or a TAFI-related polypeptide is from about 0.01 mg/day to about 500 mg/day (70-kg subject).

In one embodiment the factor VII or factor VII-related polypeptide and TAFI or TAFI-related polypeptide are present in a ratio by mass of between about 100:1 and about 1:100 (w/w factor VII:TAFI)

In one embodiment of the present invention, the pharmaceutical composition is in single-unit dosage form and consists essentially of a preparation of factor VII or a factor VII-related polypeptide, and a preparation of TAFI or a TAFI-related polypeptide, and one or more of the components selected from the list of pharmaceutical acceptable carriers, stabilizers, detergents, neutral salts, antioxidants, preservatives, and protease inhibitors.

In another embodiment of the present invention, the pharmaceutical composition is in the form of a kit-of-parts with the first-unit dosage form consisting essentially of a preparation of factor VII or a factor VII-related polypeptide, and one or more of the components selected from the list of pharmaceutical acceptable carriers, stabilizers, detergents, neutral salts, antioxidants, preservatives, and protease inhibitors; and with the second-unit dosage form consisting essentially of a preparation of TAFI or a TAFI-related polypeptide and one or more of the components selected from the list of pharmaceutical acceptable carriers, stabilizers, detergents, neutral salts, antioxidants, preservatives, and protease inhibitors.

In a further embodiment, the subject is a human; in another embodiment, the subject has an impaired thrombin generation; in one embodiment, the subject has a lowered plasma concentration of fibrinogen (e.g., a multi-transfused subject); in one embodiment, the subject has a lowered plasma concentration of factor VIII or factor IX.

In another aspect, the invention concerns a method to enhance haemostasis in a subject suffering from a factor VII responsive syndrome compared to when the subject is treated with factor VII as the only coagulation protein, the method comprising administering to the subject in need thereof a first amount of a preparation of factor VII or a factor VII-related polypeptide and a second amount of a preparation of TAFI or-a TAFI-related polypeptide, wherein the first and second amounts together are effective to enhance haemostasis.

In another aspect, the invention concerns a method to enhance formation of thrombin in a subject, the method comprising administering to the subject in need thereof a first amount of a preparation of factor VII or a factor VII-related polypeptide and a second amount of a preparation of TAFI or a TAFI-related polypeptide, wherein the first and second amounts together are effective to enhance formation of thrombin.

In another aspect, the invention concerns a method to enhance formation of thrombin in a subject suffering from a factor VII responsive syndrome compared to when the subject is treated with factor VII as the only coagulation protein, the method comprising administering to the subject in need thereof a first amount of a preparation of factor VII or a factor VII-related polypeptide and a second amount of a preparation of TAFI or a TAFI-related polypeptide, wherein the first and second amounts together are effective to enhance formation of thrombin.

In another aspect, the invention concerns a method for reducing the number of administrations of coagulation factor protein needed to accomplish haemostasis in a subject suffering from a factor VII responsive syndrome compared to the number of administrations needed when factor VII is administered to the subject as the only coagulation factor protein, the method comprising administering to a subject in need thereof a first amount of a preparation of factor VII or a factor VII-related polypeptide and a second amount of a preparation of TAFI or a TAFI-related polypeptide, wherein the first and second amounts together are effective to reduce the number of administrations of coagulation factor protein.

In another aspect, the invention concerns a method of treating bleedings in a subject suffering from a factor VII responsive syndrome, the method comprising administering to the subject in need thereof a first amount of a preparation of factor VII or a factor VII-related polypeptide and a second amount of a preparation of TAFI or a TAFI-related polypeptide, wherein the first and second amounts together are effective in treating bleedings.

In one embodiment, the factor VII is human recombinant factor VIIa (rFVIIa). In another embodiment, the rFVIIa is NOVOSEVEN® (Novo Nordisk A/S, Bagsvaerd, Demnark).

In another aspect, the invention relates to the use of factor VII or a factor VII-related polypeptide in combination with a TAFI for the manufacture of a medicament for enhancing fibrin clot formation in mammalian plasma.

In another aspect, the invention relates to a method of enhancing fibrin clot formation in a subject, which method comprises administering to a subject in need thereof a first amount of a preparation of factor VII or a factor VII-related polypeptide and a second amount of a preparation of TAFI or a TAFI-related polypeptide, wherein the first and second amounts together are effective in treating bleedings.

LIST OF FIGURES

FIG. 1: Addition of FVIIa results in a dose-dependent prolongation of the clot lysis time. This effect was optimal at 10 nM FVIIa.

Figure 2:
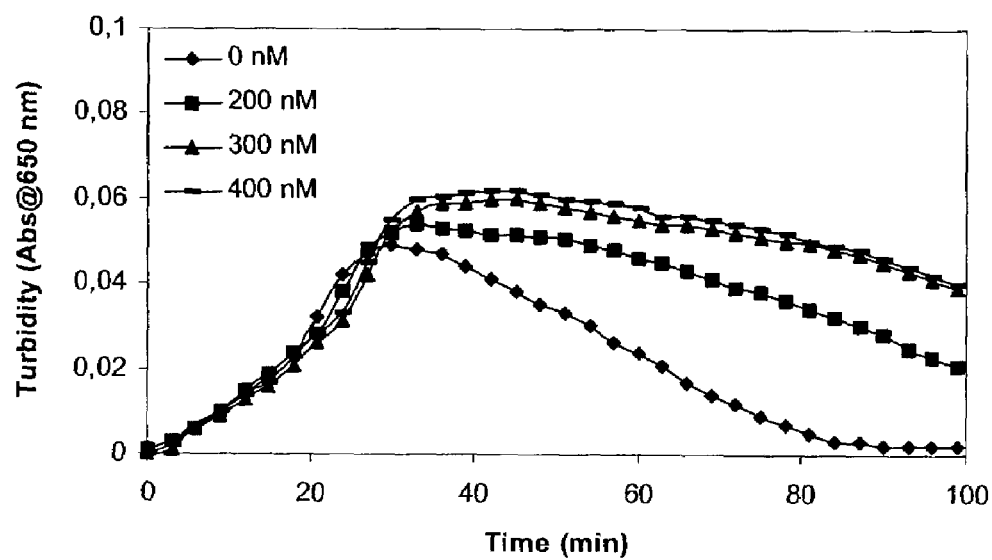

FIG. 2: In the presence of 10 nM FVIIa, addition of TAFI resulted in a further prolongation of the clot lysis time. The effect was dose-dependent and optimal at 300 nM TAFI.

Figure 3:
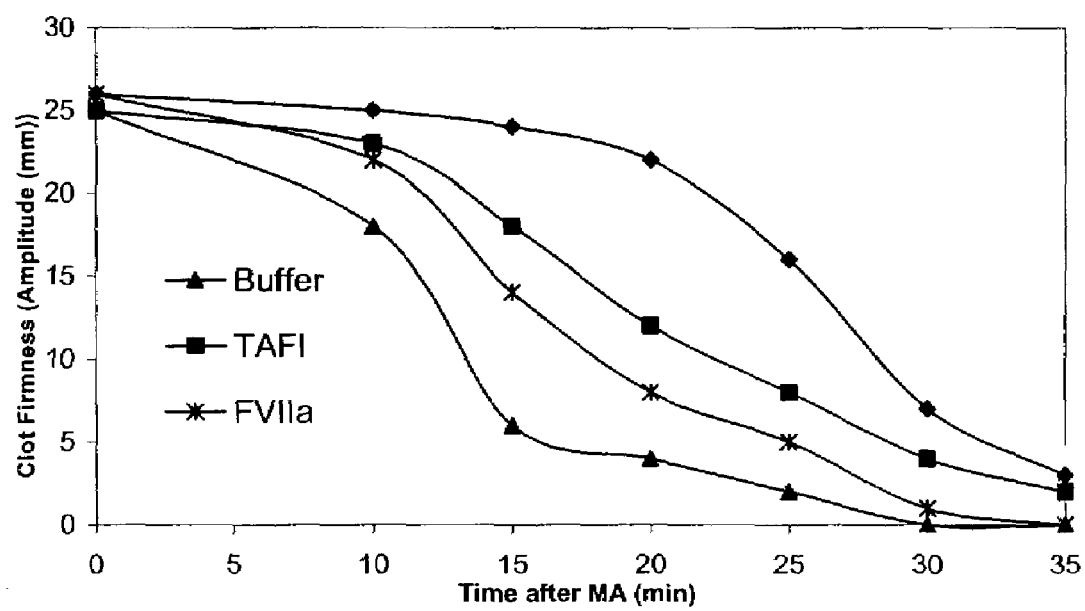

FIG. 3: Thromboelastography (roTEG) measurements were utilized to analyze the effect of FVIIa and TAFI on the Maximal Clot Firmness (MCF), as well as the clots resistance to t-PA mediated lysis.

DETAILED DESCRIPTION OF THIS INVENTION

Subjects, who bleed excessively in association with surgery or major trauma thus needing blood transfusions, develop more complications than those who do not experience any bleeding. However, also moderate bleedings may lead to complications if they require the administration of human blood or blood products (platelets, leukocytes, plasma-derived concentrates for the treatment of coagulation defects, etc.) because this is associated with the risk of transferring human viruses (e.g., hepatitis, HIV, parvovirus, or other, by now unknown viruses) as well as non-viral pathogens. Extensive bleedings requiring massive blood transfusions may lead to the development of multiple organ failure including impaired lung and kidney function. Once a subject has developed these serious complications a cascade of events involving a number of cytokines and inflammatory reactions is started making any treatment extremely difficult and unfortunately often unsuccessful. A patient experiencing a major loss of blood becomes clinically unstable. Such patients are in risk of experiencing atrial fibrillation, which may lead to a fatal stop of cardiac activity; impaired renal function; or fluid extravasations in lungs (so-called "wet lungs" or ARDS). Therefore, a major goal in surgery as well as in the treatment of major tissue damage is to avoid or minimise the bleeding. To avoid or minimize such unwanted bleedings it is important to ensure formation of stable and solid haemostatic plugs that are not readily dissolved by fibrinolytic enzymes. Furthermore, it is of importance to ensure quick and effective formation of such plugs or clots.

Subjects with thrombocytopenia (lowered count or activity of platelets) also have an impaired thrombin generation as well as a defective stabilization of the fibrin plugs resulting in haemostatic plugs prone to premature dissolution. Furthermore, subjects subjected to major trauma or organ damage and who, as a consequence, have obtained frequent blood transfusions often have lowered platelet counts as well as lowered levels of fibrinogen, factor VIII, and other coagulation proteins. These subjects experience an impaired (or lowered) thrombin generation. These subjects, therefore, have a defective, or less efficient, haemostasis leading to the formation of fibrin plugs that are easily and prematurely dissolved by proteolytic enzymes, such enzymes in addition being extensively released in situations characterized by extensive trauma and organ damage.

Bleedings in tissues may also lead to the formation of haematomas. The sizes of (in particular intercranial and spinal) haematomas are closely correlated to the extent of loss of neurological function, rehabilitation difficulties, and/or the severity and degree of permanent impairments of neurological function following rehabilitation. The most severe consequences of haematomas are seen when they are located in the brain where they may even lead to the death of the patient.

Thus, major objectives in treatment of bleedings are to obtain haemostasis in a minimum of time, thus keeping the blood loss at a minimum.

The present invention thus provides beneficial compositions, uses and methods of treatment for treatment of bleeding episodes in subjects in need of such treatment. The compositions, uses and methods may be associated with beneficial effects such as less blood loss before haemostasis is obtained, less blood needed during surgery, blood pressure kept at an acceptable level until haemostasis is obtained, faster stabilisation of blood pressure, shorter recovery time for the treated patient, shorter rehabilitation time for the treated patient, diminished formation of haematomas or formation of smaller haematomas, including haematomas in the brain, faster arrest of bleedings, reduction in the number of administrations needed to stop bleeding and maintain haemostasis.

The administration of a preparation of factor VII or a factor VII-related polypeptide, e.g., factor VIIa, in combination with a preparation of TAFI or a TAFI-related polypeptide provides a shortened clotting time, a firmer clot and an increased resistance to fibrinolysis compared to the clotting time, clot firmness and resistance when either factor VIIa or TAFI is administered alone.

The administration of a preparation of factor VII or a factor VII-related polypeptide, e.g., factor VIIa, in combination with a preparation of TAFI or a TAFI-related polypeptide also provides for a reduced time to obtain bleeding arrest and a reduced number of administrations to maintain haemostasis compared to the situation when either factor VIIa or TAFI is administered alone. The present invention provides a beneficial effect of simultaneous or sequential dosing of a preparation of TAFI or TAFI-related polypeptide and a preparation of factor VII or a factor VII-related polypeptide. The pharmaceutical composition according to the present invention may be in the form of a single composition or it may be in the form of a multi-component kit (kit-of-parts). The composition according to the present invention is useful as a therapeutic and prophylactic procoagulant in mammals, including primates such as humans. The present invention further provides a method for treating (including prophylactically treating or preventing) bleeding episodes in a subject, including a human being.

Whenever, a first or second or third, etc., unit dose is mentioned throughout this specification this does not indicate the preferred order of administration, but is merely done for convenience purposes.

A combination of a preparation of factor VII or a factor VII-related polypeptide and a preparation of TAFI or a TAFI-related polypeptide is an advantageous product ensuring short clotting times, rapid formation of haemostatic plugs, and formation of stable haemostatic plugs. It has been found by the present inventor that a combination of factor VII or a factor VII-related polypeptide and a TAFI or a TAFI-related polypeptide is an advantageous product ensuring the formation of solid, stable and quickly formed haemostatic plugs.

The present inventors have shown that a combination of factor VII or a factor VII-related polypeptide and TAFI or a TAFI-related polypeptide can increase the firmness of the clot more effectively than either factor VIIa or TAFI alone. By combining factor VII or a factor VII-related polypeptide at a concentration where no further increase in clot firmness was observed with TAFI, also at a concentration where no further increase in clot firmness was observed, it was unexpectedly shown that a further increase in clot firmness was obtained. It has also been shown that combination of factor VII or a factor VII-related polypeptide and TAFI or a TAFI-related polypeptide can prolong the in vitro clot lysis time in normal human plasma more effectively than either factor VIIa or TAFI alone. It has also been shown that combination of factor VII or a factor VII-related polypeptide and TAFI or a TAFI-related polypeptide can prolong the half-clot lysis time in normal human plasma more effectively than either factor VIIa or TAFI alone. It has also been shown that combination of factor VII or a factor VII-related polypeptide and TAFI or a TAFI-related polypeptide can protect the clot from fibrinolysis, in particular tPA-mediated fibrinolysis, in normal human plasma more effectively than either factor VIIa or TAFI alone.

Thus, by enhancing coagulation a more effective treatment of bleeding in subjects can be obtained.

Without wishing to be bound by theory, it is believed that the full thrombin generation is necessary for a solid, stabile haemostatic plug to be formed, and thereby for the maintenance of haemostasis. The fibrin structure of such a plug is dependent on both the amount of thrombin formed and the rate of the initial thrombin generation. In the presence of an impaired thrombin generation a porous fibrin plug, which is highly permeable, is being formed. The fibrinolytic enzymes normally present on the fibrin surface easily dissolve such a fibrin plug. The formation of a stable fibrin plug is also dependent on the presence of factor XIIIa, which is being activated by thrombin and therefore also dependent on the full thrombin generation. Furthermore, the recently described thrombin activatable fibrinolytic inhibitor, TAFI, requires rather high thrombin amounts for its activation. In the presence of a not fully adequate thrombin formation the TAFI may therefore not be activated resulting in the formation of a haemostatic plug, which is easier than normally dissolved by the normal fibrinolytic activity. In situations with lowered number of platelets, thrombocytopenia, a faster thrombin generation is initiated by the administration of exogenous extra factor VIIa. However, the total thrombin generation is not normalised by factor VIIa even in high concentrations.

In subjects with lowered plasma concentrations of fibrinogen (multi-transfused subjects as a consequence of multiple trauma or extensive surgery) full thrombin activation does not occur. A more effective haemostasis is then obtained by the administration of a combination of a factor VII and a TAFI.

Subjects with thrombocytopenia have an impaired thrombin generation as well as a defective stabilization of the fibrin plugs resulting in haemostatic plugs prone to premature dissolution. Furthermore, subjects subjected to major trauma or organ damage and who, as a consequence, have obtained frequent blood transfusions often have lowered platelet counts as well as lowered levels of fibrinogen, factor VIII, and other coagulation proteins. These subjects experience an impaired (or lowered) thrombin generation. In addition, their lowered fibrinogen level interfere negatively with the activation of factor XIII. These subjects, therefore, have a defective, or less efficient, haemostasis leading to the formation of fibrin plugs which are easily and prematurely dissolved by proteolytic enzymes, such enzymes in addition being extensively released in situations characterized by extensive trauma and organ damage.

In order to facilitate the formation of fully stabilized plugs with full capacity to maintain haemostasis in a subject, a composition according to the invention is administered. This composition is especially beneficial in subjects with a lowered number of platelets and in subjects with lowered plasma levels of fibrinogen and/or other coagulation proteins.

Factor VII Polypeptides:

In practicing the present invention, any factor VII polypeptide may be used that is effective in preventing or treating bleeding. This includes factor VII polypeptides derived from blood or plasma, or produced by recombinant means.

The present invention encompasses factor VII polypeptides, such as, e.g., those having the amino acid sequence disclosed in U.S. Pat. No. 4,784,950 (wild-type human factor VII). In some embodiments, the factor VII polypeptide is human factor VIIa, as disclosed, e.g., in U.S. Pat. No. 4,784,950 (wild-type factor VII). In one series of embodiments, factor VII polypeptides include polypeptides that exhibit at least about 10%, preferably at least about 30%, more preferably at least about 50%, and most preferably at least about 70%, of the specific biological activity of human factor VIIa. In one series of embodiments, factor VII polypeptides include polypeptides that exhibit at least about 90%, preferably at least about 100%, preferably at least about 120%, more preferably at least about 140%, and most preferably at least about 160%, of the specific biological activity of human factor VIIa. In one series of embodiments, factor VII polypeptides include polypeptides that exhibit at least about 70%, preferably at least about 80%, more preferably at least about 90%, and most preferable at least about 95%, of identity with the sequence of wild-type factor VII as disclosed in U.S. Pat. No. 4,784,950.

As used herein, "factor VII polypeptide" encompasses, without limitation, factor VII, as well as factor VII-related polypeptides. The term "factor VII" is intended to encompass, without limitation, polypeptides having the amino acid sequence 1-406 of wild-type human factor VII (as disclosed in U.S. Pat. No. 4,784,950), as well as wild-type factor VII derived from other species, such as, e.g., bovine, porcine, canine, murine, and salmon factor VII, said factor VII derived from blood or plasma, or produced by recombinant means. It further encompasses natural allelic variations of factor VII that may exist and occur from one individual to another. Also, degree and location of glycosylation or other post-translation modifications may vary depending on the chosen host cells and the nature of the host cellular environment. The term "factor VII" is also intended to encompass factor VII polypeptides in their uncleaved (zymogen) form, as well as those that have been proteolytically processed to yield their respective bioactive forms, which may be designated factor VIIa. Typically, factor VII is cleaved between residues 152 and 153 to yield factor VIIa.

"Factor VII-related polypeptides" include, without limitation, factor VII polypeptides that have either been chemically modified relative to human factor VII and/or contain one or more amino acid sequence alterations relative to human factor VII (i.e., factor VII variants), and/or contain truncated amino acid sequences relative to human factor VII (i.e., factor VII fragments). Such factor VII-related polypeptides may exhibit different properties relative to human factor VII, including stability, phospholipid binding, altered specific activity, and the like. The term "factor VII-related polypeptides" are intended to encompass such polypeptides in their uncleaved (zymogen) form, as well as those that have been proteolytically processed to yield their respective bioactive forms, which may be designated "factor VIIa-related polypeptides" or "activated factor VII-related polypeptides"

As used herein, "factor VII-related polypeptides" encompasses, without limitation, polypeptides exhibiting substantially the same or improved biological activity relative to wild-type human factor VII, as well as polypeptides in which the factor VIIa biological activity has been substantially modified or reduced relative to the activity of wild-type human factor VIIa. These polypeptides include, without limitation, factor VII or factor VIIa that has been chemically modified and factor VII variants into which specific amino acid sequence alterations have been introduced that modify or disrupt the bioactivity of the polypeptide.

It further encompasses polypeptides with a slightly modified amino acid sequence, for instance, polypeptides having a modified N-terminal end including N-terminal amino acid deletions or additions, and/or polypeptides that have been chemically modified relative to human factor VIIa.

Factor VII-related polypeptides, including variants of factor VII, whether exhibiting substantially the same or better bioactivity than wild-type factor VII, or, alternatively, exhibiting substantially modified or reduced bioactivity relative to wild-type factor VII, include, without limitation, polypeptides having an amino acid sequence that differs from the sequence of wild-type factor VII by insertion, deletion, or substitution of one or more amino acids.

Factor VII-related polypeptides, including variants, encompass those that exhibit at least about 10%, at least about 20%, at least about 25%, at least about 30%, at least about 40%, at least about 50%, at least about 60%, at least about 70%, at least about 75%, at least about 80%, at least about 90%, at least about 100%, at least about 110%, at least about 120%, or at least about 130%, of the specific activity of wild-type factor VIIa that has been produced in the same cell type, when tested in one or more of a clotting assay, proteolysis assay, or TF binding assay as described above.

Factor VII-related polypeptides, including variants, having substantially the same or improved biological activity relative to wild-type factor VIIa encompass those that exhibit at least about 25%, preferably at least about 50%, more preferably at least about 75%, more preferably at least about 100%, more preferably at least about 110%, more preferably at least about 120%, and most preferably at least about 130% of the specific activity of wild-type factor VIIa that has been produced in the same cell type, when tested in one or more of a clotting assay, proteolysis assay, or TF binding assay as described above.

Factor VII-related polypeptides, including variants, having substantially reduced biological activity relative to wild-type factor VIIa are those that exhibit less than about 25%, preferably less than about 10%, more preferably less than about 5% and most preferably less than about 1% of the specific activity of wild-type factor VIIa that has been produced in the same cell type when tested in one or more of a clotting assay, proteolysis assay, or TF binding assay as described above. factor VII variants having a substantially modified biological activity relative to wild-type factor VII include, without limitation, factor VII variants that exhibit TF-independent factor X proteolytic activity and those that bind TF but do not cleave factor X.

In some embodiments the factor VII polypeptides are factor VII-related polypeptides, in particular variants, wherein the ratio between the activity of said factor VII polypeptide and the activity of native human factor VIIa (wild-type FVIIa) is at least about 1.25 when tested in the "In Vitro Hydrolysis Assay" (see "Assays", below); in other embodiments, the ratio is at least about 2.0; in further embodiments, the ratio is at least about 4.0. In some embodiments of the invention, the factor VII polypeptides are factor VII-related polypeptides, in particular variants, wherein the ratio between the activity of said factor VII polypeptide and the activity of native human factor VIIa (wild-type FVIIa) is at least about 1.25 when tested in the "In Vitro Proteolysis Assay" (see "Assays", below); in other embodiments, the ratio is at least about 2.0; in further embodiments, the ratio is at least about 4.0; in further embodiments, the ratio is at least about 8.0.

In some embodiments, the factor VII polypeptide is human factor VII, as disclosed, e.g., in U.S. Pat. No. 4,784,950 (wild-type factor VII). In some embodiments, the factor VII polypeptide is human factor VIIa. In one series of embodiments, the factor VII polypeptides are factor VII-related polypeptides that exhibits at least about 10%, preferably at least about 30%, more preferably at least about 50%, and most preferably at least about 70%, of the specific biological activity of human factor VIIa. In some embodiments, the factor VII polypeptides have an amino acid sequence that differs from the sequence of wild-type factor VII by insertion, deletion, or substitution of one or more amino acids.

Non-limiting examples of factor VII variants having substantially the same or better biological activity compared to wild-type factor VIIa include, but are not limited to, those described in Danish Patent Applications Nos. PA 2000 00734 and PA 2000 01360 (corresponding to WO 01/83725), and PA 2000 01361 (corresponding to WO 02/22776). Non-limiting examples of factor VII variants having substantially the same or improved biological activity as wild-type factor VII include S52A-FVII, S60A-FVII (Iino et al., Arch. Biochem. Biophys. 352: 182-192, 1998); L305V-FVII, L305V/M306D/D309S-FVII, L305I-FVII, L305T-FVII, F374P-FVII, V158T/M298Q-FVII, V158D/ E296V/M298Q-FVII, K337A-FVII, M298Q-FVII, V158D/ M298Q-FVII, L305V/K337A-FVII, V158D/E296V/ M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/ E296V-FVII, V158D/M298K-FVII, and S336G-FVII; FVIIa variants exhibiting increased proteolytic stability as disclosed in U.S. Pat. No. 5,580,560; factor VIIa that has been proteolytically cleaved between residues 290 and 291 or between residues 315 and 316 (Mollerup et al., Biotechnol. Bioeng. 48:501-505, 1995); and oxidized forms of factor VIIa (Kornfelt et al., Arch. Biochem. Biophys. 363: 43-54, 1999). Non-limiting examples of factor VII variants having substantially reduced or modified biological activity relative to wild-type factor VII include R152E-FVIIa (Wildgoose et al., Biochem 29:3413-3420, 1990), S344A-FVIIa (Kazama et al., J. Biol. Chem. 270:66-72, 1995), FFR-FVIIa (Holst et al., Eur. J. Vasc. Endovasc. Surg. 15:515-520, 1998), and factor VIIa lacking the Gla domain, (Nicolaisen et al., FEBS Letts. 317:245-249, 1993). Non-limiting examples of chemically modified factor VII polypeptides and sequence variants are described, e.g., in U.S. Pat. No. 5,997,864.

The biological activity of factor VIIa in blood clotting derives from its ability to (i) bind to tissue factor (TF) and (ii) catalyze the proteolytic cleavage of factor IX or factor X to produce activated factor IX or X (factor IXa or Xa, respectively).

For purposes of the invention, biological activity of factor VII polypeptides ("factor VII biological activity") may be quantified by measuring the ability of a preparation to promote blood clotting using factor VII-deficient plasma and thromboplastin, as described, e.g., in U.S. Pat. No. 5,997, 864. In this assay, biological activity is expressed as the reduction in clotting time relative to a control sample and is converted to "factor VII units" by comparison with a pooled human serum standard containing 1 unit/ml factor VII activity. Alternatively, factor VIIa biological activity may be quantified by (i) Measuring the ability of factor VIIa or a factor VIIa-related polypeptide to produce activated factor X (factor Xa) in a system comprising TF embedded in a lipid membrane and factor X. (Persson et al., J. Biol. Chem. 272:19919-19924, 1997);

(ii) Measuring factor X hydrolysis in an aqueous system ("In Vitro Proteolysis Assay", see below);

(iii) Measuring the physical binding of factor VIIa or a factor VIIa-related polypeptide to TF using an instrument based on surface plasmon resonance (Persson, FEBS Letts. 413:359-363, 1997); and (iv) Measuring hydrolysis of a synthetic substrate by factor VIIa and/or a factor VIIa-related polypeptide ("In Vitro Hydrolysis Assay", see below); and (v) Measuring generation of thrombin in a TF-independent in vitro system.

The term "factor VII biological activity" or "factor VII activity" is intended to include the ability to generate thrombin; the term also includes the ability to generate thrombin on the surface of activated platelets in the absence of tissue factor.

A factor VIIa preparation that maybe used according to the invention is, without limitation, NOVOSEVEN® (Novo Nordisk A/S, Bagsvaerd, Denmark).

TAFI Polypeptides:

The present invention encompasses TAFI polypeptides, such as, e.g., those having the amino acid sequence disclosed in U.S. Pat. Nos. 5,206,161 and 5,364,934 (wild-type human TAFI).

In practicing the present invention, any TAFI polypeptide may be used that is effective in preventing or treating bleeding. This includes TAFI polypeptides derived from blood or plasma, or produced by recombinant means.

As used herein, "TAFI polypeptide" encompasses, without limitation, TAFI, as well as TAFI-related polypeptides. The term "TAFI" is intended to encompass, without limitation, polypeptides having the amino acid sequence of wild-type human TAFI (as disclosed in U.S. Pat. Nos. 5,206,161 and 5,364,934), as well as wild-type TAFI derived from other species, such as, e.g., bovine, porcine, canine, murine, and rat TAFI.

It further encompasses natural allelic variations of TAFI that may exist and occur from one individual to another. Also, degree and location of glycosylation or other post-translation modifications may vary depending on the chosen host cells and the nature of the host cellular environment. The term "TAFI" is also intended to encompass TAFI polypeptides in their uncleaved (zymogen) form, as well as those that have been proteolytically processed to yield their respective bioactive forms, which may be designated TAFIa.

"TAFI-related polypeptides" include, without limitation, TAFI polypeptides that have either been chemically modified relative to human TAFI and/or contain one or more amino acid sequence alterations relative to human TAFI (i.e., TAFI variants), and/or contain truncated amino acid sequences relative to human TAFI (i.e., TAFI fragments). Such TAFI-related polypeptides may exhibit different properties relative to human TAFI, including stability, phospholipid binding, altered specific activity, and the like.

The term "TAFI-related polypeptides" are intended to encompass such polypeptides in their uncleaved (zymogen) form, as well as those that have been processed to yield their respective bioactive forms, which may be designated "activated TAFI-related polypeptides".

As used herein, "TAFI-related polypeptides" encompasses, without limitation, polypeptides exhibiting substantially the same or improved biological activity relative to wild-type human TAFI, as well as polypeptides, in which the TAFI biological activity has been substantially modified or reduced relative to the activity of wild-type human TAFI. These polypeptides include, without limitation, TAFI or TAFIa that has been chemically modified and TAFI variants into which specific amino acid sequence alterations have been introduced that modify or disrupt the bioactivity of the polypeptide.

It further encompasses polypeptides with a slightly modified amino acid sequence, for instance, polypeptides having a modified N-terminal end including N-terminal amino acid deletions or additions, and/or polypeptides that have been chemically modified relative to human TAFI.

TAFI-related polypeptides, including variants of TAFI, whether exhibiting substantially the same or better bioactivity than wild-type TAFI, or, alternatively, exhibiting substantially modified or reduced bioactivity relative to wild-type TAFI, include, without limitation, polypeptides having an amino acid sequence that differs from the sequence of wild-type TAFI by insertion, deletion, or substitution of one or more amino acids.

TAFI-related polypeptides, including variants, encompass those that exhibit at least about 10%, at least about 20%, at least about 30%, at least about 40%, at least about 50%, at least about 60%, at least about 70%, at least about 80%, at least about 90%, at least about 100%, at least about 110%, at least about 120%, and at least about 130%, of the specific activity of wild-type TAFI that has been produced in the same cell type, when tested in the TAFI activity assay as described in the present specification.

TAFI-related polypeptides, including variants, having substantially the same or improved biological activity relative to wild-type TAFI encompass those that exhibit at least about 25%, preferably at least about 50%, more preferably at least about 75%, more preferably at least about 100%, more preferably at least about 110%, more preferably at least about 120%, and most preferably at least about 130% of the specific biological activity of wild-type human TAFI that has been produced in the same cell type when tested in one or more of the specific TAFI activity assay as described. For purposes of the invention, TAFI biological activity may be quantified by measuring the ability of a preparation to inhibit tPA-mediated clot lysis, or plasmin-mediated clot lysis, as described, e.g., in Boffa et al (J.Biol.Chem., 1998; 273: 2127-2135). In both assays, biological activity is expressed as the reduction in clot lysis time relative to a control sample. Alternatively, TAFI biological activity may be quantified by measuring hydrolysis of a synthetic substrate by TAFI or a TAFI-related polypeptide, as described, e.g., in Boffa et al (J.Biol.Chem., 1998; 273:2127-2135).

TAFI-related polypeptides, including variants, having substantially reduced biological activity relative to wild-type TAFI are those that exhibit less than about 25%, preferably less than about 10%, more preferably less than about 5% and most preferably less than about 1% of the specific activity of wild-type TAFI that has been produced in the same cell type when tested in one or more of the specific TAFI activity assays as described above.

Non-limiting examples of TAFI equivalents include plasma-derived human TAFI as described, e.g., in Bajzar et al. (J.Biol.Chem., 1995; 270:14477) or in Eaton et al. (J.Biol.Chem., 1991; 266:21833); recombinant human TAFI as described, e.g., in U.S. Pat. Nos. 5,206,161 and 5,364,934; human brain carboxypeptidase B as described, e.g., in International Publication No. WO 00/06671; pancreatic carboxypeptidase B as described, e.g., in WO 00/61727; carboxypeptidase B with a modified prodomain as described in WO 98/35988; mutated carboxypeptidase B as described in WO 97/07769; murine TAFI as described, e.g. in Marx et al. (Thromb.Haemost., 2000; 83:297-303); porcine TAFI as described, e.g., in U.S. Pat. No. 5,672,496.

In some embodiments the TAFI are TAFI equivalents wherein the ratio between the activity of said TAFI polypeptide and the activity of native human TAFI (wild-type TAFI) is at least about 1.25 when tested in the "tPA-mediated clot lysis assay" (Boffa et al, see above); in other embodiments, the ratio is at least about 2.0; in further embodiments, the ratio is at least about 4.0. In some embodiments the TAFI are TAFI equivalents wherein the ratio between the activity of said TAFI polypeptide and the activity of native human TAFI (wild-type TAFI) is at least about 1.25 when tested in the "plasmin-mediated clot lysis assay" (Boffa et al, see above); in other embodiments, the ratio is at least about 2.0; in further embodiments, the ratio is at least about 4.0.

TAFI-related polypeptides also include fragments of TAFI or TAFI-related polypeptides retaining their characteristic haemostasis-related activity. The haemostasis-related activity of TAFI or a TAFI-related polypeptide polypeptide may, for example, be measured using the TAFI-activity assay described in the present specification (Boffa et al. see above).

In preferred embodiments, the TAFI is human plasma TAFI or activated human plasma TAFIa. In another embodiment, the TAFI is recombinantly made.

Definitions

In the present context the three-letter or one-letter indications of the amino acids have been used in their conventional meaning as indicated in table 1. Unless indicated explicitly, the amino acids mentioned herein are L-amino acids. It is to be understood, that the first letter in, for example, K337 represent the amino acid naturally present at the indicated position wild-type factor VII, and that, for example, [K337A]-FVIIa designates the FVII-variant wherein the amino acid represented by the one-letter code K naturally present in the indicated position is replaced by the amino acid represented by the one-letter code A.

TABLE 1

Abbreviations for amino acids:

| Amino acid | Tree-letter code | One-letter code |
| --- | --- | --- |
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |

The term "factor VIIa" or "FVIIa" may be used interchangeably.

In this context, "subjects with an impaired thrombin generation" means subjects who cannot generate a full thrombin burst on the activated platelet surface and includes subjects having a generation of thrombin less that the thrombin-generation in subjects having a fully functioning, normal haemostatic system, including a normal amount and function of coagulation factors, platelets and fibrinogen (e.g., as in pooled, normal human plasma), and includes, without limitations, subjects lacking factor VIII; subjects having a lowered number of platelets or platelets with a defective function (e.g., thrombocytopenia or thrombasthenia Glanzmann or subjects with excessive bleeds); subjects having lowered levels of prothrombin, FX or FVII; subjects having a lowered level of several coagulation factors (e.g., due to exessive bleeding as a consequence of trauma or extensive surgery); and subjects with lowered plasma concentrations of fibrinogen (e.g., multitransfused subjects).

By "level of thrombin generation" or "normal thrombin generation" is meant the level of the patient's level of thrombin generation compared to the level in healthy subjects. The level is designated as a percentage of the normal level. The terms may, where appropriate, be used interchangeably.

The term "enhancement of the haemostatic system" means an enhancement of the ability to generate thrombin. The term "enhancing haemostasis" is intended to encompass the situations when the measured thrombin generation for a test sample containing a preparation of factor VII or a factor VII-related polypeptide and a preparation of TAFI or a TAFI-related polypeptide is prolonged relative to the individual thrombin generation of a control sample containing only the factor VII or factor VII-related polypeptide or the TAFI or TAFI-related polypeptide, respectively, when tested in the same thrombin generation assay. The thrombin generation may be assayed as described in the thrombin generation assay of the present description (see "assay part").

"Sole" agents or factors as used herein refers to situations in which the factor VII or factor VII-related polypeptide and the TAFI or TAFI-related polypeptide, taken together, are the only haemostatic agents, or active haemostatic agents, or coagulation factors contained in the pharmaceutical composition or kit, or are the only haemostatic agents,or active haemostatic agents, or coagulation factors administered to the patient in the course of a particular treatment, such as, e.g., in the course of a particular bleeding episode. It will be understood that these situations encompass those in which other haemostatic agents or coagulation factors, as applicable, are not present in either sufficient quantity or activity so as to significantly influence one or more coagulation parameters.

Clot lysis time, clot strength, fibrin clot formation, and clotting time are clinical parameters used for assaying the status of patient's haemostatic system. Blood samples are drawn from the patient at suitable intervals and one or more of the parameters are assayed by means of, e.g., thromboelastograpy as described by, e.g., Meh et al.,Blood Coagulation & Fibrinolysis 2001;12:627-637; Vig et al., Hematology, Vol. 6 (3) pp. 205-213 (2001); Vig et al., Blood coagulation & fibrinolysis, Vol. 12 (7) pp. 555-561 October (2001); Glidden et al., Clinical and applied thrombosis/hemostasis, Vol. 6 (4) pp. 226-233 October (2000); McKenzie et al., Cardiology, Vol. 92 (4) pp. 240-247 April (1999); or Davis et al., Journal of the American Society of Nephrology, Vol. 6 (4) pp. 1250-1255 (1995).

The term "prolonging clot lysis time" is intended to encompass the situations when the measured clot lysis time for a test sample containing a preparation of factor VII or a factor VII-related polypeptide and a preparation of TAFI or a TAFI-related polypeptide is prolonged relative to the individual clot lysis time of a control sample containing only the factor VII or factor VII-related polypeptide or the TAFI or TAFI-related polypeptide, respectively, when tested in the same clot lysis assay. The clot lysis time may be assayed as described above.

The term "increasing clot strength" is intended to encompass the situations when the measured clot strength, e.g., mechanical strength, for a test sample containing a preparation of factor VII or a factor VII-related polypeptide and a preparation of TAFI or a TAFI-related polypeptide is increased relative to the individual clot lysis time of a control sample containing only the factor VII or factor VII-related polypeptide or the TAFI or TAFI-related polypeptide, respectively, when tested in the same clot strength assay. The clot strength may be assayed as described, e.g. in Carr et al, 1991. (Carr M E, Zekert SL. Measurement of platelet-mediated force development during plasma clot formation. AM J MED SCI 1991; 302: 13-8), or as described above by means of thromboelastography.

The term "enhancing fibrin clot formation" is intended to encompass the situations when the measured rate for or degree of fibrin clot formation for a test sample containing a preparation of factor VII or a factor VII-related polypeptide and a preparation of a preparation of TAFI or a TAFI-related polypeptide is increased relative to the individual rate for or degree of fibrin clot formation of a control sample containing only the factor VII or factor VII-related polypeptide or the TAFI or TAFI-related polypeptide, respectively, when tested in the same clotting assay. The fibrin clot formation may be assayed as described above.

The term "shortening clotting time" is intended to encompass the situations when the measured time for clot formation (clotting time) for a test sample containing a preparation of factor VII or a factor VII-related polypeptide and a preparation of a preparation of TAFI or a TAFI-related polypeptide is increased relative to the individual clotting time of a control sample containing only the factor VII or factor VII-related polypeptide or the TAFI or TAFI-related polypeptide respectively, when tested in the same clotting assay. The clotting time may be assayed by means of standard PT og aPTT assays, which are known to the general skilled person.

The term "lowered count or activity of platelets" refers to the number of platelets (thrombocytes) present in the subject's plasma and to the biological, coagulation-related activity of such platelets. Lowered counts may be due, e.g., to increased platelet destruction, decreased platelet production, and pooling of a larger than normal fraction of platelets in the spleen. Thrombocytopenia, for example, is defined as a platelet count less than 150,000 platelets per microliter; the upper limit of the normal platelet count is generally considered to be between 350,000 and 450,000 platelets per microliter. Platelet count may be measured by automated platelet counters; this is a well known method to the skilled worker. Syndromes due to lowered platelet count include, without limitation, thrombocytopenia, coagulophathy. "Activity" includes, without limitation, aggregation, adhesion, and coagulant activity of the platelets. Decreased activity may be due, e.g., to glycoprotein abnormalities, abnormal membrane-cytoskeleton interaction, abnormalities of platelet granules, abnormalities of platelet coagulant activity, abnormalities of signal transduction and secretion. Platelet activity, including aggregation, adhesion, and coagulant activity, are measured by standard methods known to the skilled worker, see e.g.,Platelets. A Practical Approach, Ed. S. P. Watson & K. S. Authi: Clinical Aspects of Platelet Disorders (K. J. Clemetson) 15:299-318, 1996, Oxford University Press; Williams Hematology, Sixth Edition, Eds. Beutler, Lichtman, Coller, Kipps & Seligsohn, 2001, McGraw-Hill. Syndromes due to lowered platelet activity includes, without limitation, Glanzmann thrombathenis, Bernard-Soulier syndrome, anticoagulant treatment and thrombolytic treatment. "Lowered" refers to the count or activity of a sample of the test plasma compared to the count or activity in a sample of normal pooled plasma when measured in the same assay As used herein the term "bleeding disorder" reflects any defect, congenital, acquired or induced, of cellular or molecular origin that is manifested in bleeding episodes. Examples of bleeding disorders include, but are not limited to, clotting factor deficiencies (e.g. deficiency of coagulation factors VIII, IX, XI or VII), clotting factor inhibitors, defective platelet function (e.g., Glanzmann thombasthenia and Bernard-Soulier syndrome), thrombocytopenia, von Willebrand's disease, and coagulophathy such as that caused by a dilution of coagulation proteins, increased fibrinolysis and lowered number of platelets due to bleedings and/or transfusions (e.g., in multi transfused subjects having been subjected to surgery or trauma).

Bleeding refers to extravasation of blood from any component of the circulatory system. The term "bleeding episodes" is meant to include unwanted, uncontrolled and often excessive bleeding in connection with surgery, trauma, or other forms of tissue damage, as well as unwanted bleedings in subjects having bleeding disorders. Bleeding episodes may occur in subjects having a basically normal coagulation system but experiencing a (temporary) coagulophathy, as well as in subjects having congenital or acquired coagulation or bleeding disorders. In subjects having a defective platelet function, the bleedings may be likened to bleedings caused by haemophilia because the haemostatic system, as in haemophilia, lacks or has abnormal essential clotting "compounds" (e.g., platelets or von Willebrand factor protein). In subjects who experience extensive tissue damage, for example in association with surgery or vast trauma, the normal haemostatic mechanism may be overwhelmed by the demand of immediate haemostasis and they may develop excessive bleeding in spite of a basically (pre-trauma or pre-surgery) normal haemostatic mechanism. Such subjects, who further often are multi transfused, develop a (temporary) coagulopathy as a result of the bleeding and/or transfusions (i.e., a dilution of coagulation proteins, increased fibrinolysis and lowered number of platelets due to the bleeding and/or transfusions). Bleedings may also occur in organs such as the brain, inner ear region and eyes; these are areas with limited possibilities for surgical haemostasis and thus problems with achieving satisfactory haemostasis. Similar problems may arise in the process of taking biopsies from various organs (liver, lung, tumour tissue, gastrointestinal tract) as well as in laparoscopic surgery and radical retropubic prostatectomy. Common for all these situations is the difficulty to provide haemostasis by surgical techniques (sutures, clips, etc.) which also is the case when bleeding is diffuse (e.g., haemorrhagic gastritis and profuse uterine bleeding). Bleedings may also occur in subjects on anticoagulant therapy in whom a defective haemostasis has been induced by the therapy given; these bleedings are often acute and profuse. Anticoagulant therapy is often given to prevent thromboembolic disease. Such therapy may include heparin, other forms of proteoglycans, warfarin or other forms of vitamin K-antagonists as well as aspirin and other platelet aggregation inhibitors, such as, e.g., antibodies or other inhibitors of GP IIb/IIIa activity. The bleeding may also be due to so-called thrombolytic therapy which comprises combined treatment with an antiplatelet agent (e.g., acetylsalicylic acid), an anticoagulant (e.g., heparin), and a fibrinolytic agent (e.g., tissue plasminogen activator, tPA). Bleeding episodes are also meant to include, without limitation, uncontrolled and excessive bleeding in connection with surgery or trauma in subjects having acute haemarthroses (bleedings in joints), chronic haemophilic arthropathy, haematomas, (e.g., muscular, retroperitoneal, sublingual and retropharyngeal), bleedings in other tissue, haematuria (bleeding from the renal tract), cerebral haemorrhage, surgery (e.g., hepatectomy), dental extraction, and gastrointestinal bleedings (e.g., UGI bleeds). The bleeding episodes may be associated with inhibitors against factor VIII; haemophilia A; haemophilia A with inhibitors; haemophilia B; deficiency of factor VII; deficiency of TAFI; thrombocytopenia; deficiency of von Willebrand factor (von Willebrand's disease); severe tissue damage; severe trauma; surgery; laparoscopic surgery; haemorrhagic gastritis; taking biopsies; anticoagulant therapy; upper gastroentestinal bleedings (UGI); or stem cell transplantation. The bleeding episodes may be profuse uterine bleeding; occurring in organs with a limited possibility for mechanical haemostasis; occurring in the brain; occurring in the inner ear region; or occurring in the eyes. The terms "bleeding episodes" and "bleedings" may, where appropriate, be used interchangeably.

In this context, the term "treatment" is meant to include both prevention of an expected bleeding, such as, for example, in surgery, and regulation of an already occurring bleeding, such as, for example, in trauma, with the purpose of inhibiting or minimising the bleeding. The above-referenced "expected bleeding" may be a bleeding expected to occur in a particular tissue or organ, or it may be an unspecified bleeding. Prophylactic administration of a preparation of factor VII or a factor VII-related polypeptide and a preparation of TAFI or a TAFI-related polypeptide is thus included in the term "treatment".

The term "subject" as used herein is intended to mean any animal, in particular mammals, such as humans, and may, where appropriate, be used interchangeably with the term "patient". The present invention also encompasses the use of factor VII or FVII-related polypeptides, and tPA inhibitors within veterinary procedures.

The factor VII or factor VII-related polypeptides and TAFI or TAFI-related polypeptides as defined in the present specification may be administered simultaneously or sequentially. The factors may be supplied in single-dosage form wherein the single-dosage form contains both coagulation factors, or in the form of a kit-of-parts comprising a preparation of factor VII or a factor VII-related polypeptide as a first-unit dosage form and a preparation of TAFI or a TAFI-related polypeptide as a second-unit dosage form. Whenever a first or second or third, etc., unit dose is mentioned throughout this specification this does not indicate the preferred order of administration, but is merely done for convenience purposes By "simultaneous" dosing of a preparation of factor VII or a factor VII-related polypeptide and a preparation of TAFI or a TAFI-related polypeptide is meant administration of the coagulation factor proteins in single-dosage form, or administration of a first coagulation factor protein followed by administration of a second coagulation factor protein with a time separation of no more than 15 minutes, preferably 10, more preferred 5, more preferred 2 minutes. Either factor may be administered first.

By "sequential" dosing is meant administration of a first coagulation factor protein followed by administration of a second coagulation factor protein with a time separation of up to 2 hours, preferably from 1 to 2 hours, more preferred up to 1 hour, more preferred from 30 minutes to 1 hour, more preferred up to 30 minutes, more preferred from 15 to 30 minutes. Either of the two unit dosage form, or coagulation factor proteins, may be administered first. Preferably, both products are injected through the same intravenous access.

By "level of TAFI" or "TAFI level" is meant the level of the patient's clotting TAFI activity compared to the level in healthy subjects. The level is designated as a percentage of the normal level. The terms may, where appropriate, be used interchangeably.

By "reduced level of TAFI" or "reduced TAFI level" is meant a decrease in the presence or activity of TAFI in the blood stream compared to the mean TAFI level in a population of subjects having no coagulation TAFI deficiency or inhibitors to coagulation TAFI. The level of circulating TAFI can be measured by either a coagulant or an immunologic assay. TAFI procoagulant activity is determined by the ability of the patient's plasma to correct the clotting time of TAFI-deficient plasma (e.g., an APTT assay, see below; see also "assay part" of the present description).

One unit of TAFI has been defined as the amount of TAFI present in one milliliter of normal (pooled) human plasma (corresponding to a TAFI level of 100%).

One unit of factor VII is defined as the amount of factor VII present in 1 ml of normal plasma, corresponding to about 0.5 µg protein. After activation 50 units correspond to about 1 µg protein.

By "deficiency" is meant a decrease in the presence or activity of, e.g., TAFI in plasma compared to that of normal healthy individuals. The term may, where appropriate, be used interchangeably with "reduced TAFI level".

By "APTT" or "aPTT" is meant the activated partial thromboplastin time (described by, e.g., Proctor RR, Rapaport SI: The partial thromboplastin time with kaolin; a simple screening test for first-stage plasma clotting factor deficiencies. Am J Clin Pathol 36:212, 1961).

By "TAFI-responsive syndrome" is meant a syndrome where exogenous TAFI administered to the subject in need thereof may prevent, cure or ameliorate any symptoms, conditions or diseases, expected or present, caused by the syndrome. Included are, without limitation, syndromes caused by a reduced level of TAFI, e.g., bleeding disorders caused by inhibitors to TAFI. A TAFI-responsive syndrome may also be treated with a composition according to the present invention.

By "factor VII-responsive syndrome" is meant a syndrome where exogenous factor VII, preferably factor VIIa, administered to the subject in need thereof may prevent, cure or ameliorate any symptoms, conditions or diseases, expected or present, caused by the syndrome. Included are, without limitation, syndromes caused by a reduced level of clotting factors VIII, IX, XI or VII, clotting factor inhibitors, defective platelet function (e.g., Glanzmann thombasthenia and Bernard-Soulier syndrome), thrombocytopenia, von Willebrand's disease, and coagulophathy such as that caused by a dilution of coagulation proteins, increased fibrinolysis and lowered number of platelets due to bleedings and/or transfusions (e.g., in multi transfused subjects having been subjected to surgery or trauma).

"Half-life" refers to the time required for the plasma concentration of factor VII or a factor VII-related polypeptide or TAFI or a TAFI-related polypeptide to decrease from a particular value to half of that value.

By "primary haemostasis" is meant the initial generation of thrombin by FXa and TF:factor VIIa, the subsequent activation of platelets and formation of the initial loose plug of activated, adhered platelets which has not yet been stabilized by fibrin and, finally, by crosslinked fibrin. If not stabilized by the fibrin formed during the second step of the haemostatic process (maintained haemostasis), the plug is easily dissolved by the fibrinolytic system.

By "secondary haemostasis" or "maintained haemostasis" is meant the secondary, full, and major, burst or generation of thrombin taking place on the surface of activated platelets and catalysed by factor VIIIa and factor VIIIa, the subsequent formation of fibrin and the stabilization of the initial platelet plug. Stabilization of the plug by fibrin leads to full haemostasis.

By "full haemostasis" is meant the formation of a stable and solid fibrin clot or plug at the site of injury which effectively stops the bleeding and which is not readily dissolved by the fibrinolytic system. In this context, the term haemostasis will be used to represent full haemostasis as described above.

The total amount of protein in a preparation may be measured by generally known methods, e.g, by measuring optical density. Amounts of TAFI coagulation or factor VII protein ("antigen") may be measured by generally known methods such as standard Elisa immuno assays. In general terms, such assay is conducted by contacting, e.g., a solution of the TAFI protein-containing preparation with an anti-TAFI antibody immobilised onto the elisa plate, subsequently contacting the immobilised antibody-TAFI complex with a second anti TAFI antibody carrying a marker, the amounts of which, in a third step, are measured. The amounts of each coagulation factor may be measured in a similar way using appropriate antibodies. The total amount of coagulation factor protein present in a preparation is determined by adding the amounts of the individual coagulation factor proteins. In one embodiment, the preparation comprises isolated coagulation factor. In another embodiment the preparation is free of coagulation factor II and coagulation factor IIa (prothrombin and thrombin) and/or factor X or Xa.

As used herein, the term "isolated" refers to coagulation factors, e.g., TAFI or TAFI-related polypeptides that have been separated from the cell in which they were synthesized or the medium in which they are found in nature (e.g., plasma or blood). Separation of polypeptides from their cell of origin may be achieved by any method known in the art, including, without limitation, removal of cell culture medium containing the desired product from an adherent cell culture; centrifugation or filtration to remove non-adherent cells; and the like. Separation of polypeptides from the medium in which they naturally occur may be achieved by any method known in the art, including, without limitation, affinity chromatography, such as, e.g., on an anti-factor VII or anti-TAFI antibody column, respectively; hydrophobic interaction chromatography; ion-exchange chromatography; size exclusion chromatography; electrophoretic procedures (e.g., preparative isoelectric focusing (IEF)), differential solubility (e.g., ammonium sulfate precipitation), or extraction and the like.

Within the present invention an "effective amount" of factor VII or a factor VII-related polypeptide, and TAFI or a TAFI-related polypeptide is defined as the amount of factor VII or a factor VII-related polypeptide, e.g., FVIIa, and TAFI or a TAFI-related polypeptide, that together suffices to prevent or reduce bleeding or blood loss, so as to cure, alleviate or partially arrest the disease and its complications.

The term "activity of factor VIIa" or "factor VIIa-activity" includes the ability to generate thrombin; the term also includes the ability-to generate thrombin on the surface of activated platelets in the absence of tissue factor.

| | Abbreviations |
|---|---|
| TF | tissue factor |
| FVII | factor VII in its single-chain, unactivated form |
| FVIIa | factor VII in its activated form |
| rFVIIa | recombinant factor VII in its activated form |
| TAFI | TAFI in its zymogenic, unactivated form |
| TAFIa | TAFI in its activated form |
| rTAFI | recombinant TAFI |
| rTAFIa | recombinant TAFIa |

Preparation of Compounds:

Human purified factor VIIa suitable for use in the present invention is preferably made by DNA recombinant technology, e.g. as described by Hagen et al., *Proc.Natl.Acad.Sci. USA* 83: 2412-2416, 1986, or as described in European Patent No. 200.421 (ZymoGenetics, Inc.).

Factor VII may also be produced by the methods described by Broze and Majerus, *J.Biol.Chem.* 255 (4): 1242-1247, 1980 and Hedner and Kisiel, *J.Clin.Invest.* 71: 1836-1841, 1983. These methods yield factor VII without detectable amounts of other blood coagulation factors. An even further purified factor VII preparation may be obtained by including an additional gel filtration as the final purification step. factor VII is then converted into activated factor VIIa by known means, e.g. by several different plasma proteins, such as TAFIIa, IX a or Xa. Alternatively, as described by Bjoern et al. (Research Disclosure, 269 September 1986, pp.564-565), factor VII may be activated by passing it through an ion-exchange chromatography column, such as Mono Q® (Pharmacia fine Chemicals) or the like.

Factor VII-related polypeptides may produced by modification of wild-type factor VII or by recombinant technology. factor VII-related polypeptides with altered amino acid sequence when compared to wild-type factor VII may be produced by modifying the nucleic acid sequence encoding wild-type factor VII either by altering the amino acid codons or by removal of some of the amino acid codons in the nucleic acid encoding the natural factor VII by known means, e.g. by site-specific mutagenesis.

It will be apparent to those skilled in the art that substitutions can be made outside the regions critical to the function of the factor VIIa or TAFI-molecule and still result in an active polypeptide. Amino acid residues essential to the activity of the factor VII or factor VII-related polypeptide or TAFI or TAFI-related polypeptide, and therefore preferably not subject to substitution, may be identified according to procedures known in the art, such as site-directed mutagenesis or alanine-scanning-mutagenesis (see, e.g., Cunningham and Wells, 1989, *Science* 244: 1081-1085). In the latter technique, mutations are introduced at every positively charged residue in the molecule, and the resultant mutant molecules are tested for coagulant, respectively cross-linking activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The introduction of a mutation into the nucleic acid sequence to exchange one nucleotide for another nucleotide may be accomplished by site-directed mutagenesis using any of the methods known in the art. Particularly useful is the procedure that utilizes a super coiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI, which is specific for methylated and hemimethylated DNA to digest the parental DNA template and to select for mutation-containing synthesized DNA. Other procedures known in the art for creating, identifying and isolating variants may also be used, such as, for example, gene shuffling or phage display techniques.

Separation of polypeptides from their cell of origin may be achieved by any method known in the art, including, without limitation, removal of cell culture medium containing the desired product from an adherent cell culture; centrifugation or filtration to remove non-adherent cells; and the like.

Optionally, factor VII or factor VII-related polypeptides may be further purified. Purification may be achieved using any method known in the art, including, without limitation, affinity chromatography, such as, e.g., on an anti-factor VII antibody column (see, e.g., Wakabayashi et al., J. Biol. Chem. 261:11097, 1986; and Thim et al., Biochem. 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, Protein Purification, Springer-Verlag, New York, 1982; and Protein Purification, J. C. Janson and Lars Ryden, editors, VCH Publishers, New York, 1989. Following purification, the preparation preferably contains less than about 10% by weight, more preferably less than about 5% and most preferably less than about 1%, of non-factor VII or factor VII-related polypeptides derived from the host cell.

Factor VII or factor VII-related polypeptides may be activated by proteolytic cleavage, using TAFIIa or other proteases having trypsin-like specificity, such as, e.g., factor IXa, kallikrein, factor Xa, and thrombin. See, e.g., Osterud et al., Biochem. 11:2853 (1972); Thomas, U.S. Pat. No. 4,456,591; and Hedner et al., J. Clin. Invest. 71:1836 (1983). Alternatively, factor VII or factor VII-related polypeptides may be activated by passing it through an ion-exchange chromatography column, such as Mono Q® (Pharmacia) or the like. The resulting activated factor VII or factor VII-related polypeptide may then be formulated and administered as described below.

TAFI for use within the present invention may be isolated from plasma according to known methods, such as those disclosed by (Bajzar et al., J. Biol. Chem. 270:14477, 1995). It is preferred, however, to use recombinant TAFI so as to avoid to the use of blood- or tissue-derived products that carry a risk of disease transmission. Methods for preparing recombinant TAFI are known in the art; see, for example, Boffa et al., J. Biol Chem. 273:2127, 1998, and Eaton et al., J. Biol. Chem. 266: 21833, 1991. Activated TAFI is described in, for example, International Publication No. WO 96/23064 (Biotechnology General). TAFI variants may be produced by means of site-directed mutagenesis as described above.

TAFI-related polypeptides may produced by modification of wild-type TAFI or by recombinant technology. TAFI-related polypeptides with altered amino acid sequence when compared to wild-type TAFI may be produced by modifying the nucleic acid sequence encoding wild-type TAFI either by altering the amino acid codons or by removal of some of the amino acid codons in the nucleic acid encoding the natural TAFI by known means, e.g. by site-specific mutagenesis, as described in more detail above. Separation of polypeptides from their cell of origin may be achieved by any method known in the art, including, without limitation, removal of cell culture medium containing the desired product from an adherent cell culture; centrifugation or filtration to remove non-adherent cells; and the like. Optionally, TAFI or TAFI-related polypeptides may be further purified. Purification may be achieved using any method known in the art, including, without limitation, affinity chromatography, such as, e.g., on an anti-TAFI anti-body column; hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like, as described in more detail above. Following purification, the preparation preferably contains less than about 10% by weight, more preferably less than about 5% and most preferably less than about 1%, of non-TAFI or TAFI-related polypeptides derived from the host cell. The resulting activated TAFI or TAFI-related polypeptide may then be formulated and administered as described below.

As will be appreciated by those skilled in the art, it is preferred to use TAFI polypeptides and Factor VII polypeptides syngeneic with the subject in order to reduce the risk of inducing an immune response. Preparation and characterization of non-human TAFI has been disclosed by, for example, Marx et al., Thromb. Haemost. 83:297, 2000. The present invention also encompasses the use of such TAFI and factor VIIa proteins within veterinary procedures.

Pharmaceutical Compositions and Methods of Use

The preparations of the present invention may be used to treat any factor VII responsive syndrome, such as, e.g., bleeding disorders, including, without limitation, syndromes caused by a reduced level of clotting factors VIII, IX, XI or VII, clotting factor inhibitors, defective platelet function (e.g., Glanzmann thombasthenia and Bernard-Soulier syndrome), thrombocytopenia, von Willebrand's disease, and coagulophathy such as that caused by a dilution of coagulation proteins, increased fibrinolysis and lowered number of platelets due to bleedings and/or transfusions (e.g., in multi transfused subjects having been subjected to surgery or trauma). Pharmaceutical compositions comprising a preparation of factor VII or a factor VII-related polypeptide and a preparation of TAFI or a TAFI-related polypeptide according to the present invention are primarily intended for parenteral administration for prophylactic and/or therapeutic treatment. Preferably, the pharmaceutical compositions are administered parenterally, i.e., intravenously, subcutaneously, or intramuscularly; intravenously being most preferred. They may also be administered by continuous or pulsatile infusion.

Pharmaceutical compositions or formulations according to the invention comprise a factor VII or a factor VII-related polypeptide, and TAFI or a TAFI-related polypeptide, either formulated in a single-unit dosage form or in the form of a kit-of parts, preferably dissolved in, a pharmaceutically acceptable carrier, preferably an aqueous carrier or diluent. Briefly, pharmaceutical compositions suitable for use according to the present invention is made by mixing factor VII or a factor VII-related polypeptide, or TAFI or a TAFI-related polypeptide, or factor VII or a factor VII-related polypeptide in combination with a TAFI, preferably in purified form, with suitable adjuvants and a suitable carrier or diluent. A variety of aqueous carriers may be used, such as water, buffered water, 0.4% saline, 0.3% glycine and the like. The preparations of the invention can also be formulated using non-aqueous carriers, such as, e.g., in the form of a gel or as liposome preparations for delivery or targeting to the sites of injury. Liposome preparations are generally described in, e.g., U.S. Pat. Nos. 4,837,028, 4,501, 728, and 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

Formulations may further include one or more diluents, emulsifiers, preservatives, buffers, excipients, etc. and may be provided in such forms as liquids, powders, emulsions, controlled release, etc. One skilled in this art may formulate the compositions of the invention an appropriate manner, and in accordance with accepted practices, such as those disclosed in *Remington's Pharmaceutical Sciences*, Gennaro, ed., Mack Publishing Co., Easton, Pa., 1990. Thus, a typical pharmaceutical composition for intravenous infusion could be made up to contain 250 ml of sterile Ringer's solution and 10 mg of the preparation.

The compositions containing the preparations of the present invention can be administered for prophylactic and/or therapeutic treatments. In therapeutic applications, compositions are administered to a subject already suffering from a disease, as described above, in an amount sufficient to cure, alleviate or partially arrest the clinical manifestations of the disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix.

Local delivery of the preparations of the present invention, such as, for example, topical application, may be carried out, e.g., by means of a spray, perfusion, double balloon catheters, stent, incorporated into vascular grafts or stents, hydrogels used to coat balloon catheters, or other well established methods. In any event, the pharmaceutical compositions should provide a quantity of the preparation sufficient to effectively treat the condition.

The concentration of factor VII or factor VII-related polypeptide, TAFI or TAFI-related polypeptide, or factor VII or factor VII-related polypeptide in combination with TAFI or TAFI-related polypeptide in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected. Administration by injection or infusion, in particular injection, is preferred. Thus, the factor VII or factor VII-related polypeptide and the TAFI or TAFI-related polypeptide are prepared in a form suitable for intravenous administration, such as a preparation that is either a dissolved lyophilized powder or a liquid formulation containing both the factor VII or factor VII-related polypeptide and the TAFI or TAFI-related polypeptide in one dosage form, or a dissolved lyophilized powder or a liquid formulation containing the factor VII or factor VII-related polypeptide in one dosage form and dissolved lyophilized powder or a liquid formulation containing the TAFI or TAFI-related polypeptide in another dosage form.

It is to be understood that the amount of factor VII or factor VII-related polypeptide and the amount of TAFI or TAFI-related polypeptide together comprise an aggregate effective amount for treating the bleeding episode.

It must be kept in mind that the materials of the present invention may generally be employed in serious disease or injury states, that is, life threatening or potentially life threatening situations. In such cases, in view of the minimization of extraneous substances and general lack of immunogenicity of factor VIIa and TAFI in humans, it is possible and may be felt desirable by the treating physician to administer a substantial excess of these compositions.

In prophylactic applications, compositions containing a preparation of factor VII or a factor VII-related polypeptide and a preparation of TAFI or a TAFI-related polypeptide are administered to a subject susceptible to or otherwise at risk of a disease state or injury to enhance the subject's own coagulative capability. Such an amount is defined to be a "prophylactically effective dose." It is to be understood that the amount of factor VII or factor VII-related polypeptide and the amount of TAFI or TAFI-related polypeptide together comprise an aggregate effective amount for preventing a bleeding episode.

Single or multiple administrations of the compositions can be carried out with dose levels and patterns being selected by the treating physician. The compositions may be administered one or more times per day or week. An effective amount of such a pharmaceutical composition is the amount that provides a clinically significant effect against bleeding episodes. Such amounts will depend, in part, on the particular condition to be treated, age, weight, and general health of the subject, and other factors evident to those skilled in the art.

The composition of the invention is generally administered in a single dose before the expected bleeding or at the start of the bleeding. It may however also be given repeatedly (in multiple doses) preferably with intervals of 2-4-6-12 hour, depending on the dose given and the condition of the subject.

For treatment in connection with deliberate interventions, the factor VII or factor VII-related polypeptide and the TAFI or TAFI-related polypeptide will typically be administered within about 24 hours prior to performing the intervention, and for as much as 7 days or more thereafter. Administration as a coagulant can be by a variety of routes as described herein.

The composition may be in the form of a single preparation (single-dosage form) comprising both a preparation of a preparation of factor VII or a factor VII-related polypeptide and a preparation of a preparation of TAFI or a TAFI-related polypeptide in suitable concentrations. The composition may also be in the form of a kit-of-parts consisting of a first-unit dosage form comprising a preparation of a preparation of factor VII or a factor VII-related polypeptide and a second-unit dosage form comprising a preparation of a preparation of TAFI or a TAFI-related polypeptide. In this case, the factor VII or factor VII-related polypeptide and the TAFI or TAFI-related polypeptide should be administered one after the other, preferably within about 15 minutes of each other, for example within 10 minutes of each other or, preferably, within 5 minutes or, more preferred, within 2 minutes of each other. Either of the two unit dosage forms can be administered first.

The kit includes at least two separate pharmaceutical compositions. The kit includes container means for containing the separate compositions such as a divided bottle or a divided foil packet. Typically the kit includes directions for the administration of the separate components. The kit form is particularly advantageous when the separate components are preferably administered in different dosage forms, are administered at different dosage intervals, or when titration of the individual components of the combination is desired by the prescribing physician.

The amount of factor VII or factor VII-related polypeptide and the amount of TAFI or TAFI-related polypeptide administered according to the present invention may vary from a ratio of between about 1:100 to about 100:1 (w/w). The ratio of factor VII to TAFI may thus be, e.g., about 1:100, or 1:90, or 1:80, or 1:70 or 1:60, or 1:50, or 1:40, or 1:30, or 1:20, or 1:10, or 1:5, or 1:2, or 1:1, or 2:1, or 5:1, or 10:1, or 20:1, or 30.1, or 40:1, or 50:1, or 60:1, or 70:1, or 80:1, or 90:1, or 100:1, or between about 1:90 to about 1:1, or between about 1:80 to about 1:2, or between about 1:70 to about 1:5, or between about 1:60 to about 1:10, or between about 1:50 to about 1:25, or between about 1:40 to about 1:30, or between about 90:1 to about 1:1, or between about 80:1 to about 2:1, or between about 70:1 to about 5:1, or between about 60:1 to about 10:1, or between about 50:1 to about 25:1, or between about 40:1 to about 30:1.

The dose of the factor VII or factor VII-related polypeptide ranges from what corresponds to about 0.05 mg to about 500 mg/day of wild-type factor VII, e.g., from about 1 mg to about 200 mg/day, or, e.g., from about 5 mg to about 175 mg/day for a 70-kg subject as loading and maintenance doses, depending on the weight of the subject, the condition and the severity of the condition.

The dose of the TAFI or TAFI-related polypeptide ranges from what corresponds to about 0.05 mg to about 500 mg/day of wild-type TAFI, e.g., from about 1 mg to about 200 mg/day, or, e.g., from about 1 mg to about 175 mg/day for a 70-kg subject as loading and maintenance doses, depending on the weight of the subject, the condition and the severity of the condition.

The combination of factor VII or a factor VII-related polypeptide, and TAFI shows a synergistic effect in an in vitro clot firmness- and fibrinolysis time-assay. Moreover, the combination of factor VII or a factor VII-related polypeptide and TAFI shows a synergistic effect in forming stable fibrin clots, increasing the half-clot lysis time, increasing clot strength and increasing resistance to fibrinolysis.

The composition may be in the form of a single preparation comprising both factor VII or a factor VII-related polypeptide, and TAFI or a TAFI-related polypeptide in suitable concentrations. The composition may also be in the form of a kit consisting of a first-unit dosage form comprising factor VII or a factor VII-related polypeptide and a second-unit dosage form comprising TAFI or a TAFI-related polypeptide and, optionally, one or more further unit dosage forms comprising a factor VIII and/or an TFPI inhibitor. In this case, the factor VIIa and the TAFI should be administered sequentially, preferably within about 1-2 hours of each other, for example within 30 minutes of each other or, preferably, within 10 minutes or, more preferred, within 5 minutes of each other. Either of the two unit dosage forms can be administered first.

Since the present invention relates to the prevention or treatment of bleeding episodes or for coagulative treatment by treatment with a combination of active ingredients that may be administered separately, the invention also relates to combining separate pharmaceutical compositions in kit form. The kit includes at least two separate pharmaceutical compositions. The kit includes container means for containing the separate compositions such as a divided bottle or a divided foil packet. Typically the kit includes directions for the administration of the separate components. The kit form is particularly advantageous when the separate components are preferably administered in different dosage forms, are administered at different dosage intervals, or when titration of the individual components of the combination is desired by the prescribing physician Assays:

Test for Factor VIIa Activity:

A suitable assay for testing for factor VIIa activity and thereby selecting suitable factor VIIa variants can be performed as a simple preliminary in vitro test:

In Vitro Hydrolysis Assay

Native (wild-type) factor VIIa and factor VIIa variant (both hereafter referred to as "factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to factor VIIa (final concentration 100 nM) in 50 mM Hepes, pH 7.4, containing 0.1 M NaCl, 5 mM CaCl$_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of variant and wild-type factor VIIa:

Ratio=($A_{405\ nm}$ factor VIIa variant)/($A_{405\ nm}$ factor VIIa wild-type).

Based thereon, factor VIIa variants with an activity comparable to or higher than native factor VIIa may be identified, such as, for example, variants where the ratio between the activity of the variant and the activity of native factor VII (wild-type FVII) is around, versus above 1.0.

The activity of factor VIIa or factor VIIa variants may also be measured using a physiological substrate such as factor X, suitably at a concentration of 100-1000 nM, where the factor Xa generated is measured after the addition of a suitable chromogenic substrate (eg. S-2765). In addition, the activity assay may be run at physiological temperature.

In Vitro Proteolysis Assay

Native (wild-type) factor VIIa and factor VIIa variant (both hereafter referred to as "factor VIIa") are assayed in parallel to directly compare their specific activities. The assay is carried out in a microtiter plate (MaxiSorp, Nunc, Denmark). factor VIIa (10 nM) and factor X (0.8 microM) in 100 microL 50 mM Hepes, pH 7.4, containing 0.1 M NaCl, 5 mM CaCl2 and 1 mg/ml bovine serum albumin, are incubated for 15 min. factor X cleavage is then stopped by the addition of 50 microL 50 mM Hepes, pH 7.4, containing 0.1 M NaCl, 20 mM EDTA and 1 mg/ml bovine serum albumin. The amount of factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of variant and wild-type factor VIIa:

Ratio=($A$405 nm factor VIIa variant)/($A$405 nm factor VIIa wild-type).

Based thereon, factor VIIa variants with an activity comparable to or higher than native factor VIIa may be identified, such as, for example, variants where the ratio between the activity of the variant and the activity of native factor VII (wild-type FVII) is around, versus above 1.0.

Thrombin Generation Assay:

The ability of factor VII or factor VII-related polypeptides or TAFI or TAFI-related polypeptides (e.g., variants) to generate thrombin can be measured in an assay comprising all relevant coagulation factors and inhibitors at physiological concentrations and activated platelets (as described on p. 543 in Monroe et al. (1997) Brit. J. Haematol. 99, 542-547 which is hereby incorporated as reference).

Test for TAFI Activity:

Suitable assays for testing for TAFI activity, and thereby providing means for selecting suitable TAFI variants for use in the present invention, can be performed as simple in vitro tests as described, for example, in Boffa et al., J. Biol Chem. 273:2127, 1998 (the "TAFI assay").

The present invention is further illustrated by the following examples, which, however, are not to be construed as limiting the scope of protection. The features disclosed in the foregoing description and in the following examples may, both separately and in any combination thereof, be material for realizing the invention in diverse forms thereof.

EXAMPLES

Example 1

Improving Haemostatic Clot Stability by Combining Coagulation Factors VIIa and TAFI Methods:

Clot lysis assay: Normal human plasma diluted 10-fold with buffer (20 mM HEPES, 150 mM NaCl, 5 mM CaCl, pH 7.4) containing Innovin (Dade Behring, 2000-fold dilution), rFVIIa (Novo Nordisk A/S, Bagsvaerd, Denmark; various concentrations) and t-PA (American Diagnostics, 8 nM) was added to 96-well ELISA plates and turbidity at 650 nm was measured over time at room temperature. Where indicated, purified human TAFI (Bajzar et al., J. Bioæ Chem. 270: 14477, 1995, various concentrations) was included.

Rotatonal thromboelastography (roTEG): Measurements was conducted on citrated normal human plasma added 5 nM t-PA and the effect of addition of 1 nM FVIIa alone or in combination with 30 nM TAFI was analyzed. Clotting was initiated by addition of Innovin (final concentration 2000-fold diluted, Dade Behring #526945) and calcium (final concentration 15 mM) in a 20 mM HEPES, 150 mM NaCl, pH 7.4 buffer.

Results:

Clot lysis assay: Addition of FVIIa results in a dose-dependent prolongation of the clot lysis time (FIG. 1). This effect was optimal at 10 nM FVIIa. In the presence of 10 nM FVIIa, addition of TAFI resulted in a further prolongation of the clot lysis time (FIG. 2). The effect was dose-dependent and optimal at 300 nM TAFI.

Thromboelastography: roTEG measurements were utilized to analyze the effect of FVIIa and TAFI on the Maximal Clot Firmness (MCF), as well as the clots resistance to t-PA mediated lysis. Prior to addition of FVIIa/TAFI, the MCF was 25 mm and the time required for half clot lysis was 12.3 minutes (FIG. 3). Addition of TAFI (300 nM) did not alter MCF but prolonged the half-clot lysis time to 20.5 min (FIG. 3). Similarly, addition of FVIIa (1 nM) resulted in clot protection from t-PA-mediated fibrinolysis (half-clot lysis time; 16.7 min) without any effect on MCF (FIG. 3). However, addition of FVIIa (1 nM) together with TAFI increases the half-clot lysis time to 27.2 min, FIG. 3).

CONCLUSION

These results demonstrate that FVIIa and TAFI addition to plasma improve clot mechanical strength and resistance to t-PA mediated fibrinolysis.

The invention claimed is:

1. A pharmaceutical composition containing an effective amount for treating bleeding episodes in a subject in need thereof comprising: (i) factor VII polypeptide, and (ii) human TAFI polypeptide.

2. The pharmaceutical composition according to claim 1, wherein the factor VII polypeptide is human factor VII.

3. The pharmaceutical composition according to claim 2, wherein the human factor VII is in its activated form.

4. The pharmaceutical composition according to claim 2, wherein the human factor VII is recombinant human factor VII.

5. The pharmaceutical composition according to claim 4, wherein the recombinant human factor VII is in its activated form.

6. The pharmaceutical composition according to claim 1, wherein the human TAFI polypeptide is in its activated form.

7. The pharmaceutical composition according to claim 1, wherein the human TAFI polypeptide is recombinant human TAFI.

8. The pharmaceutical composition according to claim 7, wherein the recombinant human TAFI is in its activated form.

9. The pharmaceutical composition according to claim 1, wherein the factor VII polypeptide is selected from: bovine, porcine, canine, equine, murine or salmon factor VII.

10. The pharmaceutical composition according to claim 1, wherein the factor VII polypeptide is derived from plasma or blood.

11. The pharmaceutical composition according to claim 1, wherein the factor VII polypeptide and the human TAFI polypeptide are in activated forms.

12. The pharmaceutical composition according to claim 1, wherein the factor VII polypeptide and the human TAFI polypeptide are present in a ratio of between about 100:1 and about 1:100 (w/w factor VII:TAFI).

13. The pharmaceutical composition according to claim 1, further comprising one or more pharmaceutically acceptable excipients suitable for injection or infusion.

14. A kit of parts containing a treatment for bleeding episodes in a subject in need thereof comprising:
   a) an effective amount of a preparation of factor VII polypeptide and a pharmaceutically acceptable carrier in a first-unit dosage form;
   b) an effective amount of a preparation of human TAFI polypeptide and a pharmaceutically acceptable carrier in a second-unit dosage form; and
   c) a container suitable for containing said first-unit and second-unit dosage forms.

15. The kit of parts according to claim 14, wherein the factor VII polypeptide is human factor VII.

16. The kit of parts according to claim 15, wherein the human factor VII is in its activated form.

17. The kit of parts according to claim 15, wherein the human factor VII is recombinant human factor VII.

18. The kit of parts according to claim 17, wherein the recombinant human factor VII is in its activated form.

19. The kit of parts according to claim 14, wherein the human TAFI polypeptide is in its activated form.

20. The kit of parts according to claim 14, wherein the human TAFI polypeptide is recombinant human TAFI.

21. The kit of parts according to claim 20, wherein the recombinant human TAFI is in its activated form.

22. The kit of parts according to claim 14, wherein the factor VII polypeptide is selected from: bovine, porcine, canine, equine, murine or salmon factor VII.

23. The kit of parts according to claim 14, wherein the factor VII polypeptide is derived from plasma.

24. The kit of parts according to claim 14, wherein the factor VII polypeptide and the human TAFI polypeptide are in activated forms.

25. The kit of parts to claim 14, wherein the factor VII polypeptide and the human TAFI polypeptide are present in a ratio of between about 100:1 and about 1:100 (w/w factor VII:TAFI).

26. The kit of parts according to claim 14, further comprising one or more pharmaceutically acceptable excipients suitable for injection or infusion.

27. A kit containing a treatment for bleeding episodes comprising
   a) an effective amount of a preparation of (I) factor VII polypeptide, (II) an effective amount of human TAFI polypeptide, and (III) a pharmaceutically acceptable carrier in a single-unit dosage form; and
      b) a container suitable for containing said single-unit dosage form.

28. The kit of parts according to claim 27, wherein the factor VII polypeptide is human factor VII.

29. The kit of parts according to claim 28, wherein the human factor VII is in its activated form.

30. The kit of parts according to claim 28, wherein the human factor VII is recombinant human factor VII.

31. The kit of parts according to claim 30, wherein the recombinant human factor VII is in its activated form.

32. The kit of parts according to claim 27, wherein the human TAFI polypeptide is in its activated form.

33. The kit of parts according to claim 27, wherein the human TAFI polypeptide is recombinant human TAFI.

34. The kit of parts according to claim 33, wherein the recombinant human TAFI is in its activated form.

35. The kit of parts according to claim 27, wherein the factor VII polypeptide is selected from: bovine, porcine, canine, equine, murine or salmon factor VII.

36. The kit of parts according to claim 27, wherein the factor VII polypeptide is derived from plasma.

37. The kit of parts according to claim 27, wherein the factor VII polypeptide and the human TAFI polypeptide are in activated forms.

38. The kit of parts to claim 27, wherein the factor VII polypeptide and the human TAFI polypeptide are present in a ratio of between about 100:1 and about 1:100 (w/w factor VII:TAFI).

39. The kit of parts according to claim 27, further comprising one or more pharmaceutically acceptable excipients suitable for injection or infusion.

40. A pharmaceutical composition containing an effective amount for treating bleeding episodes in a subject in need thereof comprising: (i) a factor VII-related polypeptide and (ii) human TAFI polypeptide, wherein the factor VII-related polypeptide is selected from the group consisting of: S52A-factor VIIa, S60A-factor VIIa, L305V-factor VIIa, L305V/M306D/D309S-factor VIIa, L305I-factor VIIa, L305T-factor VIIa, F374P-factor VIIa, V158T/M298Q-factor VIIa, V158D/E296V/M298Q-factor VIIa, K337A-factor VIIa, M298Q-factor VIIa, V158D/M298Q-factor VIIa, L305V/K337A-factor VIIa, V158D/E296V/M298Q/L305V-factor VIIa, V158D/E296V/M298Q/K337A-factor VIIa, V158D/E296V/M298Q/L305V/K337A-factor VIIa, K157A-factor VIIa, E296V-factor VIIa, E296V/M298Q-factor VIIa, V158D/E296V-factor VIIa, V158D/M298K-factor VIIa, S336G-factor VIIa, a factor VII variant, a factor VIIa polypeptide that has been proteolytically cleaved between residues 290 and 291 or between residues 315 and 316, and oxidized forms of factor VIIa.

41. The pharmaceutical composition according to claim 40, wherein the factor VII-related polypeptide is in its activated form.

42. The pharmaceutical composition according to claim 40, wherein the human TAFI polypeptide is in its activated form.

43. The pharmaceutical composition according to claim 40, wherein the human TAFI polypeptide is recombinant human TAFI.

44. The pharmaceutical composition according to claim 43, wherein the recombinant human TAFI is in its activated form.

45. The pharmaceutical composition according to claim 40, wherein the factor VII variant selected from the group consisting of: selected from the group consisting of V158D/E296V/M298Q-factor VIIa, M298Q-factor VIIa, and V158D/L296V/M298Q/K337A-factor VIIa.

46. The pharmaceutical composition according to claim 40, wherein the factor VII-related polypeptide and the human TAFI polypeptide are in activated forms.

47. The pharmaceutical composition according to claim 40, wherein the factor VII-related polypeptide and the human TAFI polypeptide are present in a ratio of between about 100:1 and about 1:100 (w/w factor VII:TAFI).

48. The pharmaceutical composition according to claim 40, wherein the ratio between the activity of the factor VII-related polypeptide and the activity of native human factor VIIa is at least about 1.25 when tested in an In Vitro Hydrolysis Assay.

49. The pharmaceutical composition according to claim 40, further comprising one or more pharmaceutically acceptable excipients suitable for injection or infusion.

50. A kit of parts containing a treatment for bleeding episodes in a subject in need thereof comprising:
  a) an effective amount of a preparation of a factor VII-related polypeptide, wherein the factor VII-related polypeptide is selected from the group consisting of: S52A-factor VIIa, S60A-factor VIIa, L305V-factor VIIa, L305V/M306D/D309S-factor VIIa, L305I-factor VIIa, L305T-factor VIIa, F374P-factor VIIa, V158T/M298Q-factor VIIa, V158D/E296V/M298Q-factor VIIa, K337A-factor VIIa, M298Q-factor VIIa, V158D/M298Q-factor VIIa, L305V/K337A-factor VIIa, V158D/E296V/M298Q/L305V-factor VIIa, V158D/E296V/M298Q/K337A-factor VIIa, V158D/E296V/M298Q/L305V/K337A-factor VIIa, K157A-factor VIIa, E296V-factor VIIa, E296V/M298Q-factor VIIa, V158D/E296V-factor VIIa, V158D/M298K-factor VIIa, S336G-factor VIIa, a factor VII variant, a factor VIIa polypeptide that has been proteolytically cleaved between residues 290 and 291 or between residues 315 and 316, and oxidized forms of factor VIIa and a pharmaceutically acceptable carrier in a first-unit dosage form;
  b) an effective amount of a preparation of human TAFI polypeptide and a pharmaceutically acceptable carrier in a second-unit dosage form; and
  c) a container suitable for containing said first-unit and second-unit dosage forms.

51. The kit of parts according to claim 50, wherein the factor VII-related polypeptide is in its activated form.

52. The kit of parts according to claim 50, wherein the human TAFI polypeptide is in its activated form.

53. The kit of parts according to claim 50, wherein the human TAFI polypeptide is recombinant human TAFI.

54. The kit of parts according to claim 53, wherein the recombinant human TAFI is in its activated form.

55. The kit of parts according to claim 50, wherein the factor VII variant selected from the group consisting of: selected from the group consisting of V158D/E296V/M298Q-factor VIIa, M298Q-factor VIIa, and V158D/E296V/M298Q/K337A-factor VIIa.

56. The kit of parts according to claim 50, wherein the factor VII-related polypeptide and the human TAFI polypeptide are in activated forms.

57. The kit of parts to claim 50, wherein the factor VII polypeptide or factor VII-related polypeptide and the human TAFI polypeptide are present in a ratio of between about 100:1 and about 1:100 (w/w factor VII:TAFI).

58. The kit of parts according to claim 50, wherein the ratio between the activity of the factor VII-related polypeptide and the activity of native human factor VIIa is at least about 1.25 when tested in an In Vitro Hydrolysis Assay.

59. The kit of parts according to claim 50, further comprising one or more pharmaceutically acceptable excipients suitable for injection or infusion.

60. A kit containing a treatment for bleeding episodes in a subject in need thereof comprising
  a) (I) an effective amount of a preparation of a factor VII-related polypeptide, wherein the factor VII-related polypeptide is selected from the group consisting of: S52A-factor VIIa, S60A-factor VIIa, L305V-factor VIIa, L305V/M306D/D309S-factor VIIa, L305I-factor VIIa, L305T-factor VIIa, F374P-factor VIIa, V158T/M298Q-factor VIIa, V158D/E296V/M298Q-factor VIIa, K337A-factor VIIa, M298Q-factor VIIa, V158D/M298Q-factor VIIa, L305V/K337A-factor VIIa, V158D/E296V/M298Q/L305V-factor VIIa, V158D/E296V/M298Q/K337A-factor VIIa, V158D/E296V/M298Q/L305V/K337A-factor VIIa, K157A-factor VIIa, E296V-factor VIIa, E296V/M298Q-factor VIIa, V158D/E296V-factor VIIa, V158D/M298K-factor VIIa, S336G-factor VIIa, a factor VII variant, a factor VIIa polypeptide that has been proteolytically cleaved between residues 290 and 291 or between residues 315 and 316, and oxidized forms of factor VIIa, (II) an effective amount of human TAFI polypeptide, and (III) a pharmaceutically acceptable carrier in a single-unit dosage form; and
  b) a container suitable for containing said single-unit dosage form.

61. The kit of parts according to claim 60, wherein the factor VII-related polypeptide is in its activated form.

62. The kit of parts according to claim 60, wherein the human TAFI polypeptide is in its activated form.

63. The kit of parts according to claim 60, wherein the human TAFI polypeptide is recombinant human TAFI.

64. The kit of parts according to claim 63, wherein the recombinant human TAFI is in its activated form.

65. The kit of parts according to claim 63, wherein the factor VII-related polypeptide is a factor VII variant selected from the group consisting of: selected from the group consisting of V158D/E296V/M298Q-factor VIIa, M298Q-factor VIIa, and V158D/E296V/M298Q/K337A-factor VIIa.

66. The kit of parts according to claim 60, wherein the factor VII-related polypeptide and the human TAFI polypeptide are in activated forms.

67. The kit of parts to claim 60, wherein the factor VII-related polypeptide and the human TAFI polypeptide are present in a ratio of between about 100:1 and about 1:100 (w/w factor VII :TAFI).

68. The kit of parts according to claim 60, further comprising one or more pharmaceutically acceptable excipients suitable for injection or infusion.

* * * * *